(12) United States Patent
Flint

(10) Patent No.: US 9,408,629 B2
(45) Date of Patent: Aug. 9, 2016

(54) METHOD AND APPARATUS FOR DIRECTED DEVICE PLACEMENT IN THE CEREBRAL VENTRICLES OR OTHER INTRACRANIAL TARGETS

(71) Applicant: Alexander C. Flint, Menlo Park, CA (US)

(72) Inventor: Alexander C. Flint, Menlo Park, CA (US)

(73) Assignee: Bedrock Inventions, LLC, Menlo Park, CA (US)

( * ) Notice: Subject to any disclaimer, the term of this patent is extended or adjusted under 35 U.S.C. 154(b) by 0 days.

(21) Appl. No.: 14/637,007

(22) Filed: Mar. 3, 2015

(65) Prior Publication Data

US 2015/0173793 A1 Jun. 25, 2015

Related U.S. Application Data

(62) Division of application No. 12/479,255, filed on Jun. 5, 2009, now Pat. No. 9,039,615.

(60) Provisional application No. 61/059,371, filed on Jun. 6, 2008.

(51) Int. Cl.
*A61B 17/34* (2006.01)
*A61B 8/08* (2006.01)
(Continued)

(52) U.S. Cl.
CPC ........... *A61B 17/3423* (2013.01); *A61B 8/0808* (2013.01); *A61B 8/12* (2013.01);
(Continued)

(58) Field of Classification Search
CPC .... A61B 17/3423; A61B 19/201; A61B 8/12; A61B 8/0808; A61B 8/00; A61B 8/4209; A61B 2019/208; A61B 2019/5276; A61M 27/006; A61M 2205/04; A61M 2210/0693
See application file for complete search history.

(56) References Cited

U.S. PATENT DOCUMENTS

| 3,017,887 A | 1/1962 | Heyer |
| 3,021,842 A | 2/1962 | Flood |

(Continued)

FOREIGN PATENT DOCUMENTS

| WO | WO 98/51229 A1 | 11/1998 |
| WO | WO 99/16374 A1 | 4/1999 |

OTHER PUBLICATIONS

International Search Report for PCT Appl. No. PCT/US2009/046482, mailed Jan. 13, 2010.
(Continued)

*Primary Examiner* — Bo J Peng
(74) *Attorney, Agent, or Firm* — Bill Kennedy Patents; Bill Kennedy

(57) ABSTRACT

Apparatus for directed cranial access to a site includes a guidepiece and a receptacle. The receptacle includes a lower part having a rim and a base, and a hollow stem at the base adapted to be mounted in a hole in the skull; and an upper part having a rim and an opening at the top. Each part of the receptacle has an interior spherical surface, and they can be joined at the rims to form an inner surface enclosing a spherical interior. The guidepiece includes a body having a spherical outer surface and a cylindrical bore through the center, defining an alignment axis; and a guide tube in the bore. The guidepiece is dimensioned to fit rotatably within the receptacle interior, and the apparatus is assembled by joining the receptacle over the guidepiece body, with the guide tube projecting through the top opening. The guide tube is dimensioned to accept an imaging device such as an ultrasound probe during an imaging stage, and an adaptor is provided, dimensioned to accept a device to be placed at the site during a placement stage. The probe is inserted into the guide tube and the guidepiece is swiveled until the image shows that the alignment axis is aligned along an optimal trajectory to the site, the receptacle is tightened to lock the guidepiece, and the imaging device is withdrawn. Then the adaptor is inserted into the guide tube, and the device is inserted through the adaptor along the established trajectory to the site. After placement of the device into the intracranial target, the adaptor, guidepiece, and receptacle are removed as a unit over the device while the device is held in place.

21 Claims, 13 Drawing Sheets

(51) Int. Cl.
*A61B 8/12* (2006.01)
*A61M 27/00* (2006.01)
*A61B 8/00* (2006.01)

(52) U.S. Cl.
CPC ............ *A61B 90/11* (2016.02); *A61M 27/006* (2013.01); *A61B 8/00* (2013.01); *A61B 8/4209* (2013.01); *A61B 2090/103* (2016.02); *A61B 2090/378* (2016.02); *A61M 2205/04* (2013.01); *A61M 2210/0693* (2013.01)

(56) References Cited

U.S. PATENT DOCUMENTS

| | | | |
|---|---|---|---|
| 3,135,263 A | | 6/1964 | Connelley |
| 3,460,537 A | | 8/1969 | Zies |
| 4,613,324 A | * | 9/1986 | Ghajar ............... A61B 17/3403 604/264 |
| 4,681,103 A | | 7/1987 | Boner et al. |
| 4,809,694 A | * | 3/1989 | Ferrara .............. A61B 17/3403 606/130 |
| 5,263,956 A | | 11/1993 | Nobles |
| 5,352,207 A | * | 10/1994 | Nussbaum .......... A61M 27/006 600/561 |
| 5,690,117 A | | 11/1997 | Gilbert |
| 6,328,694 B1 | * | 12/2001 | Michaeli ................ A61B 5/031 600/438 |
| 6,328,748 B1 | | 12/2001 | Hennig |
| 6,382,865 B1 | | 5/2002 | Paxman |
| 6,988,696 B2 | | 1/2006 | Attee |
| 7,717,853 B2 | | 5/2010 | Nita |
| 2002/0019641 A1 | | 2/2002 | Truwit |
| 2004/0267284 A1 | * | 12/2004 | Parmer ................ A61B 19/201 606/130 |
| 2007/0038100 A1 | * | 2/2007 | Nita .................... A61B 5/6864 600/439 |
| 2007/0083100 A1 | | 4/2007 | Schulz-Stubner |

OTHER PUBLICATIONS

Masuzawa, H., et al., "Intraoperative Ultrasonography Through a Burr-Hole", Acta Neurochirigica 77, 1985, pp. 41-45.

Enzmann, D.R., et al., "Intraoperative and outpatient electroencephalography through a burr-hole", Neuroradiology, 26, 1984, pp. 57-59.

Craniotomy, 2009 Mayfield Clinic, Cincinnati, Ohio, downloaded May 6, 2009 from www.mayfieldclinic.com (http://www.mayheldclinic.com/PE-Craniotomy.htm).

* cited by examiner

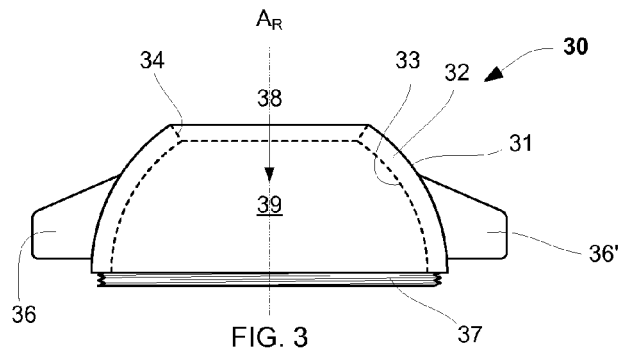
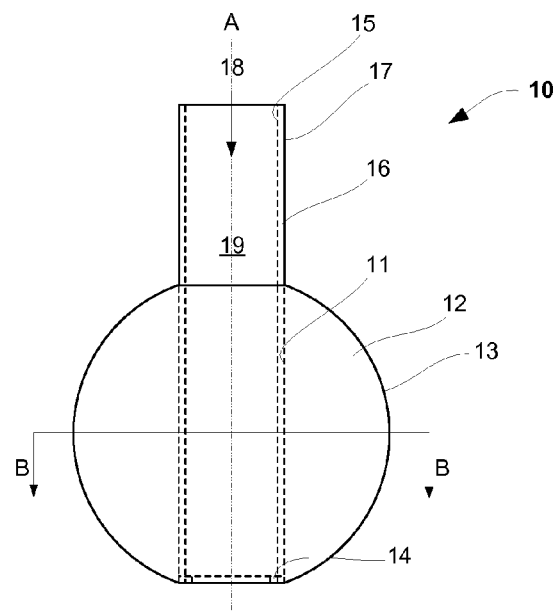
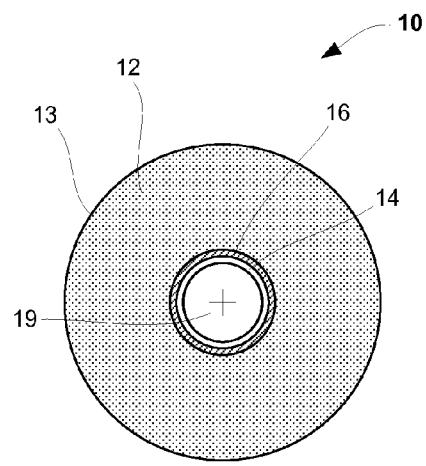
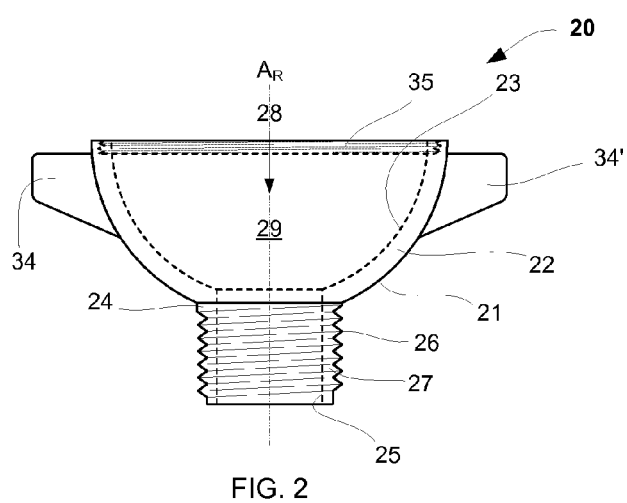

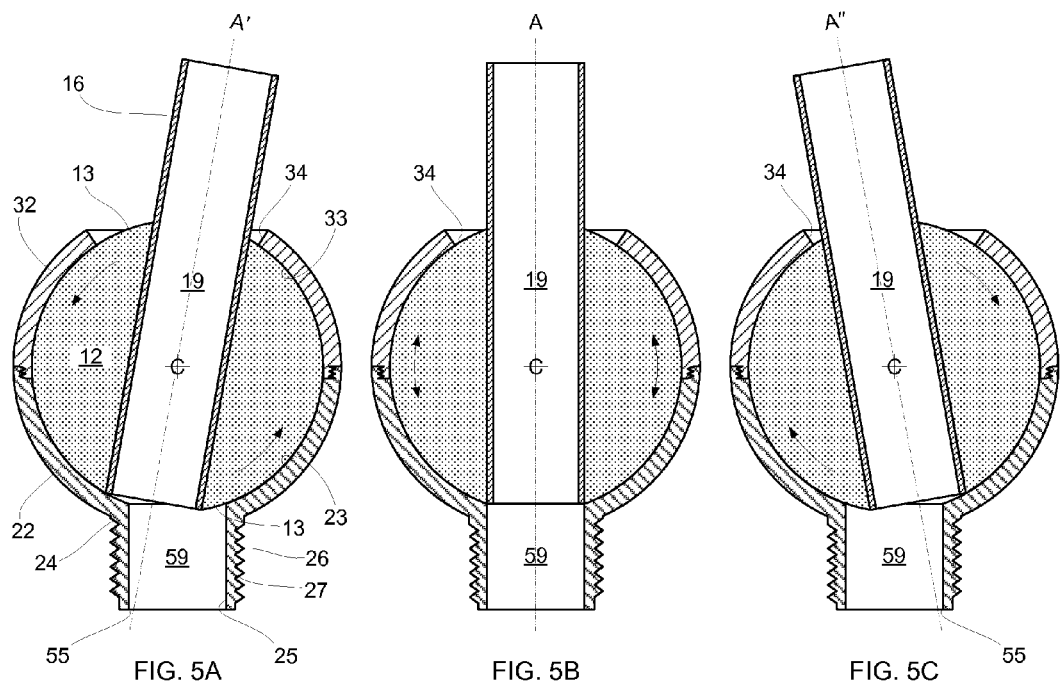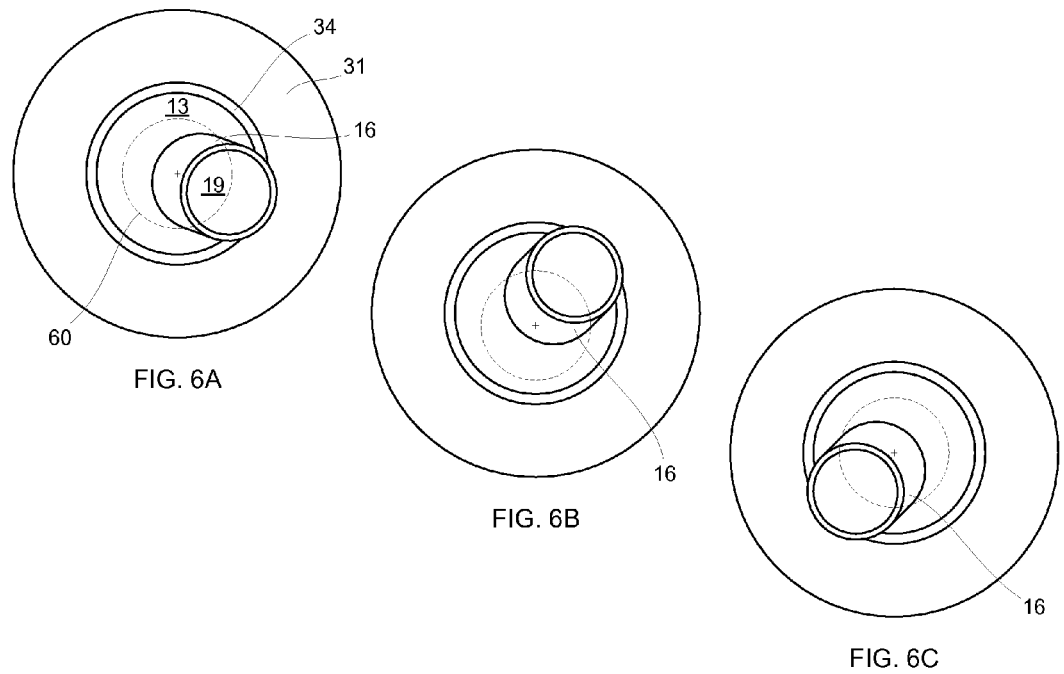

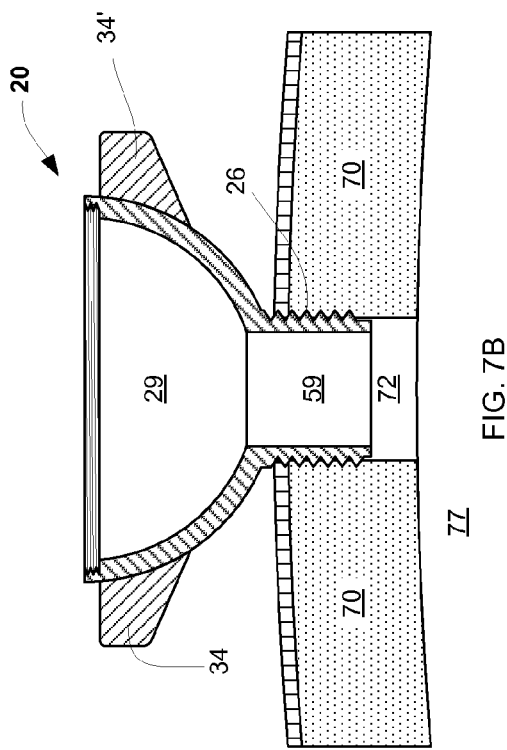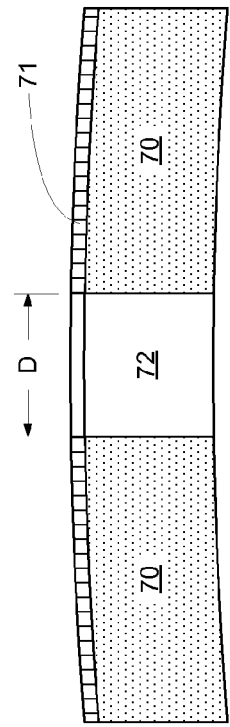

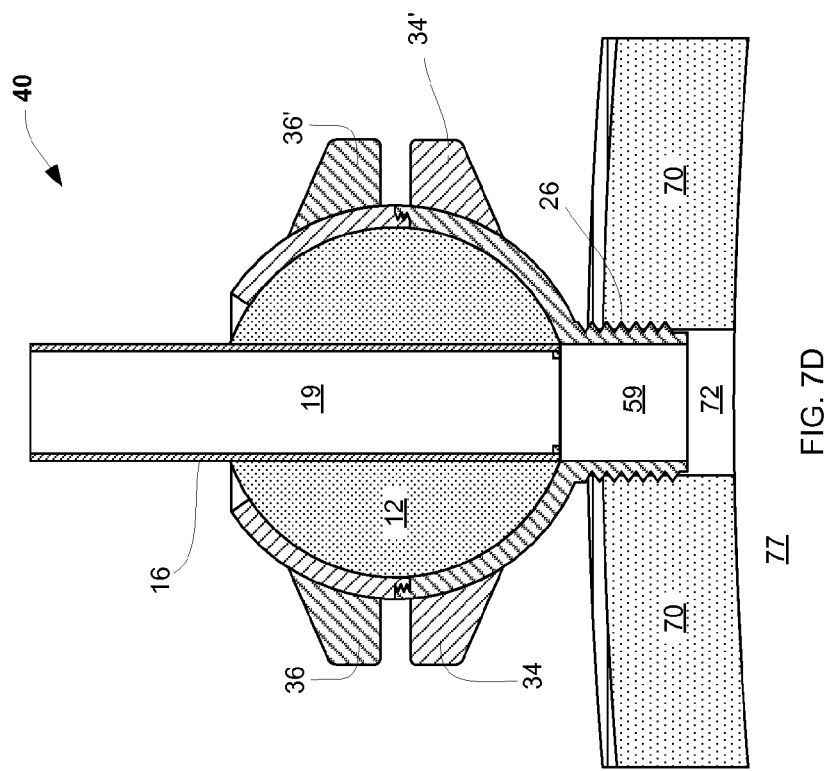
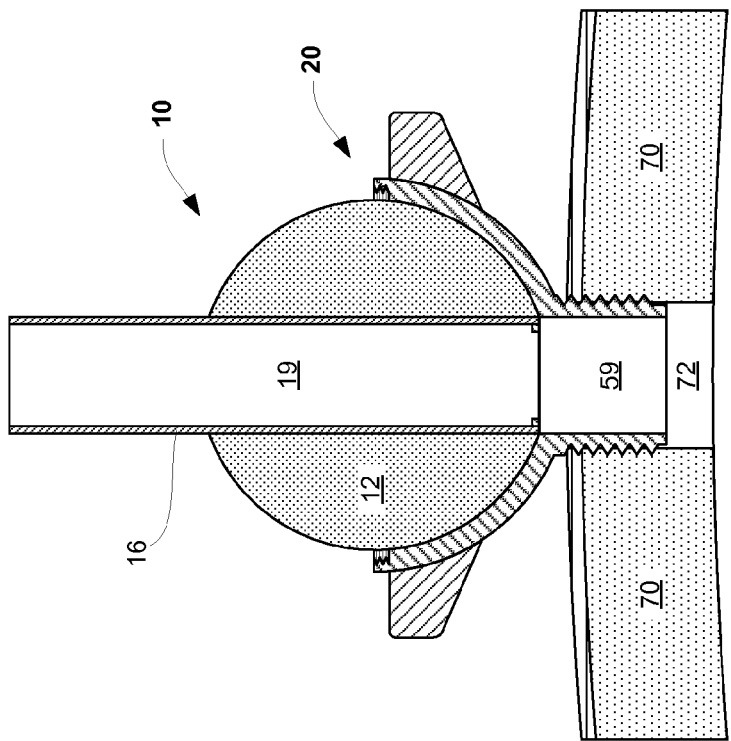

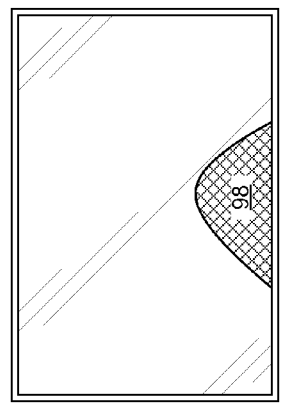
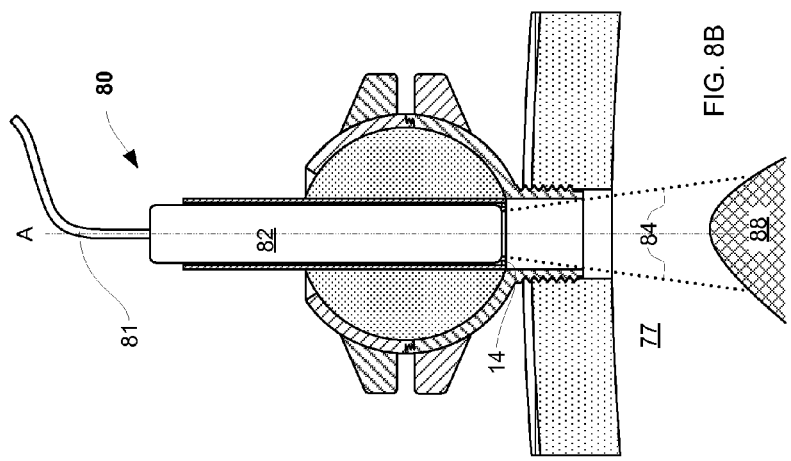
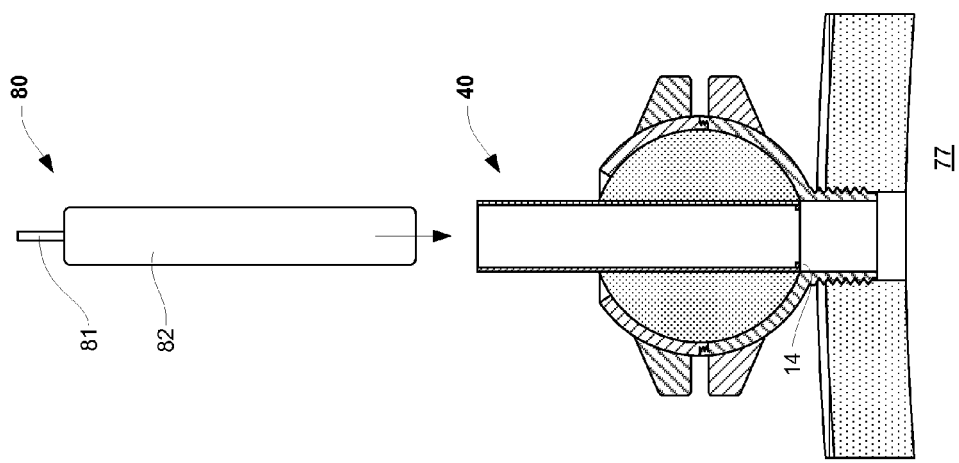

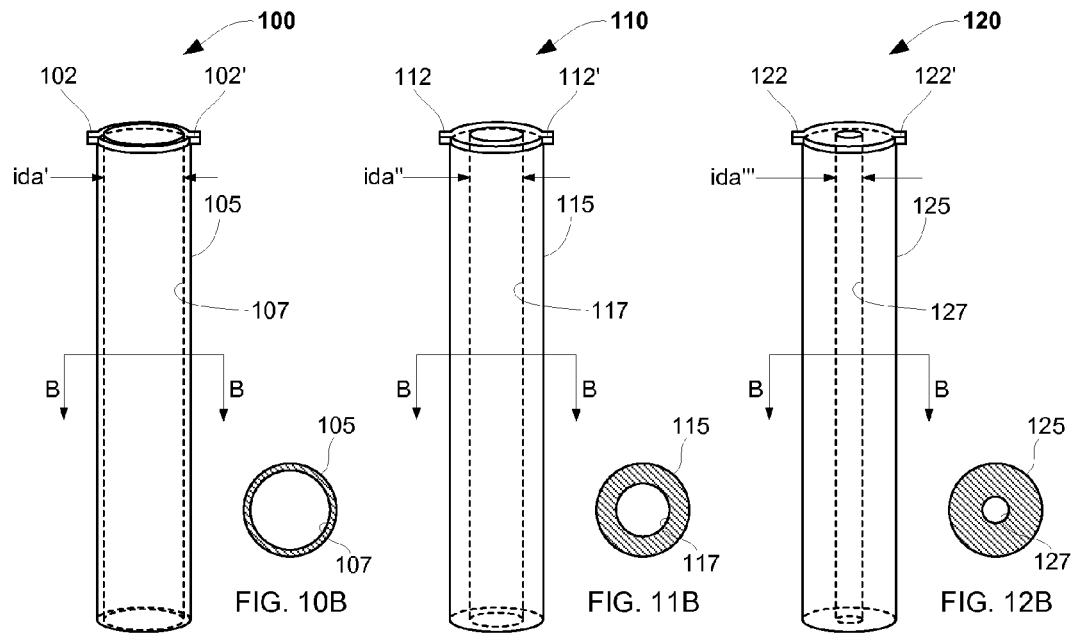
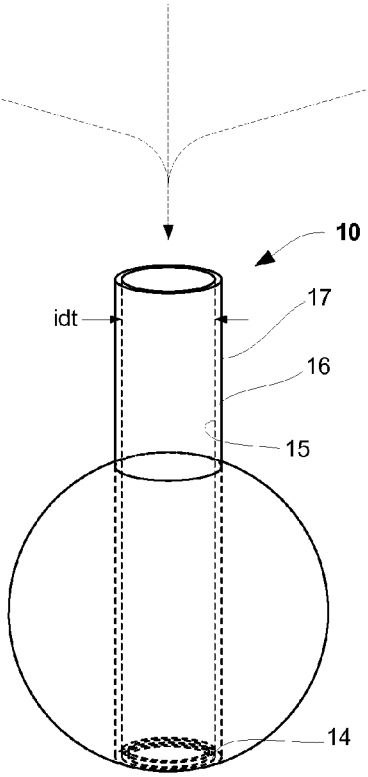
FIG. 10A  FIG. 11A  FIG. 12A
FIG. 13

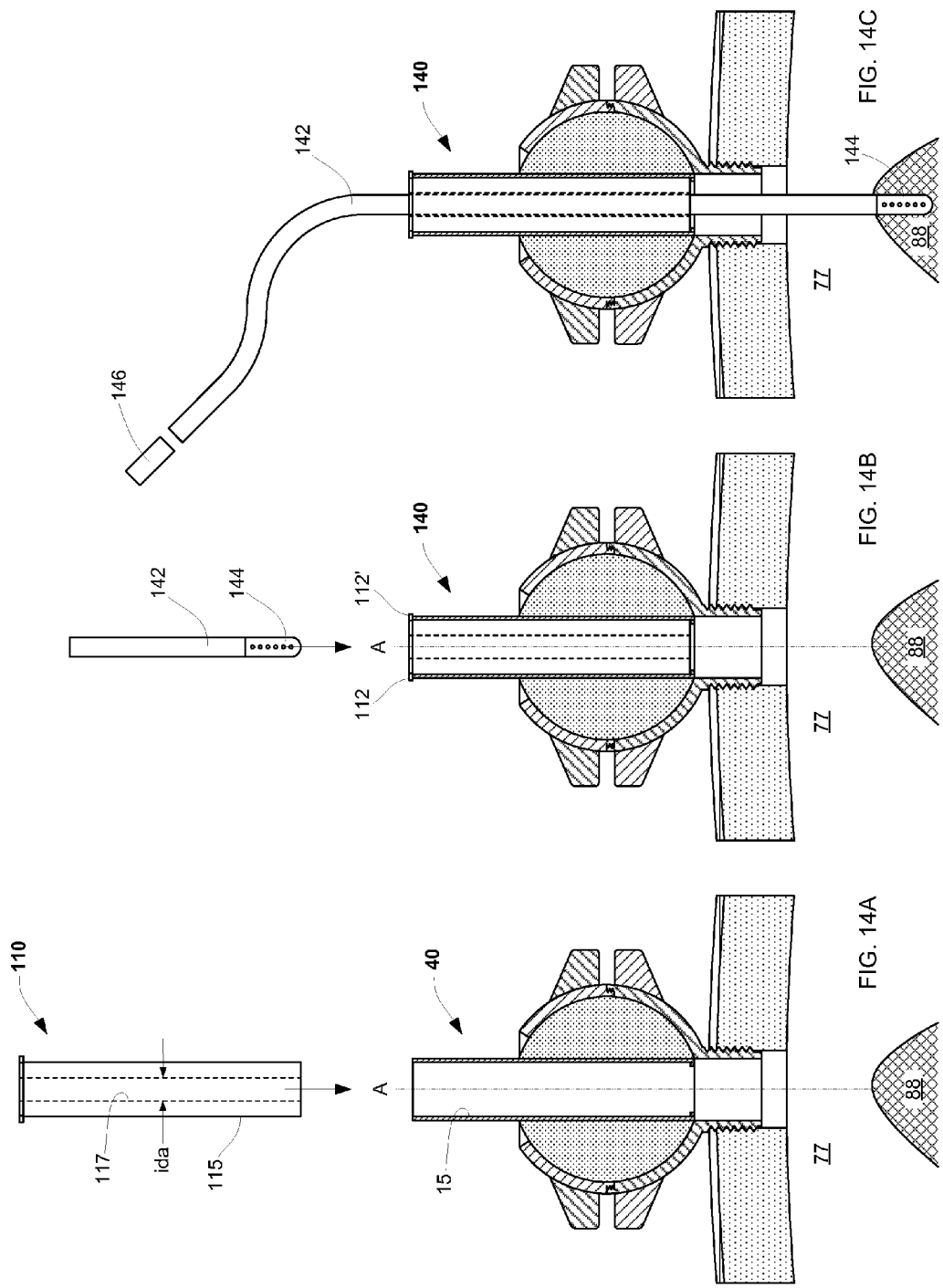

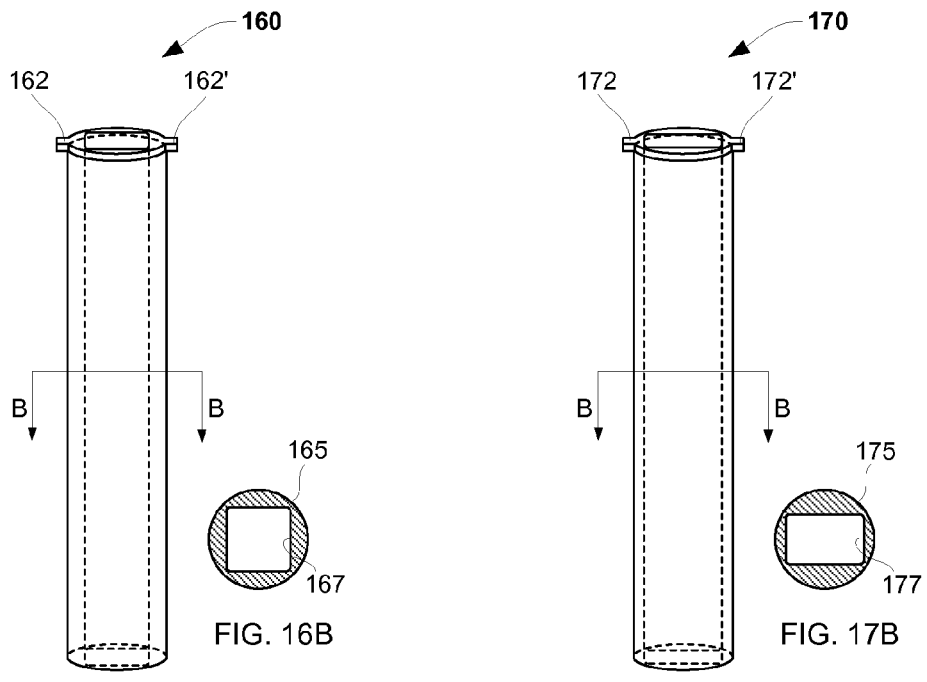
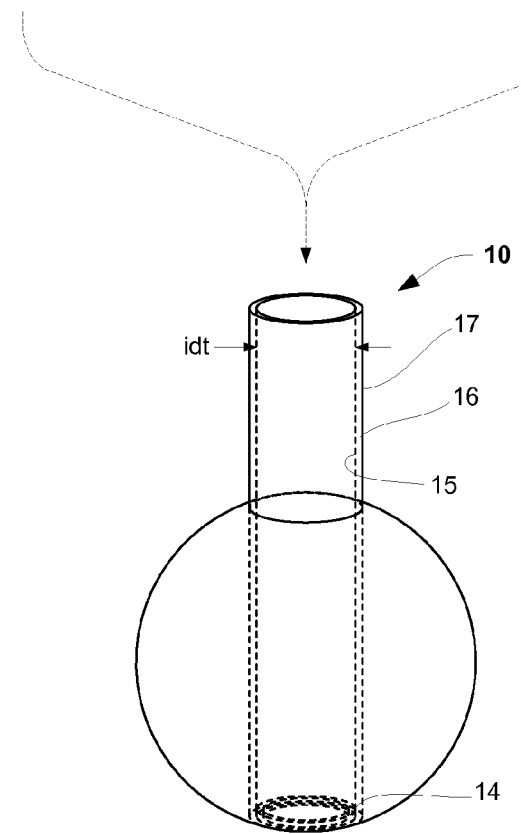
FIG. 18

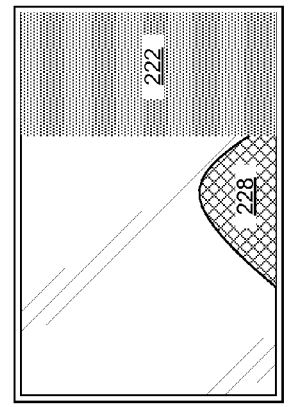
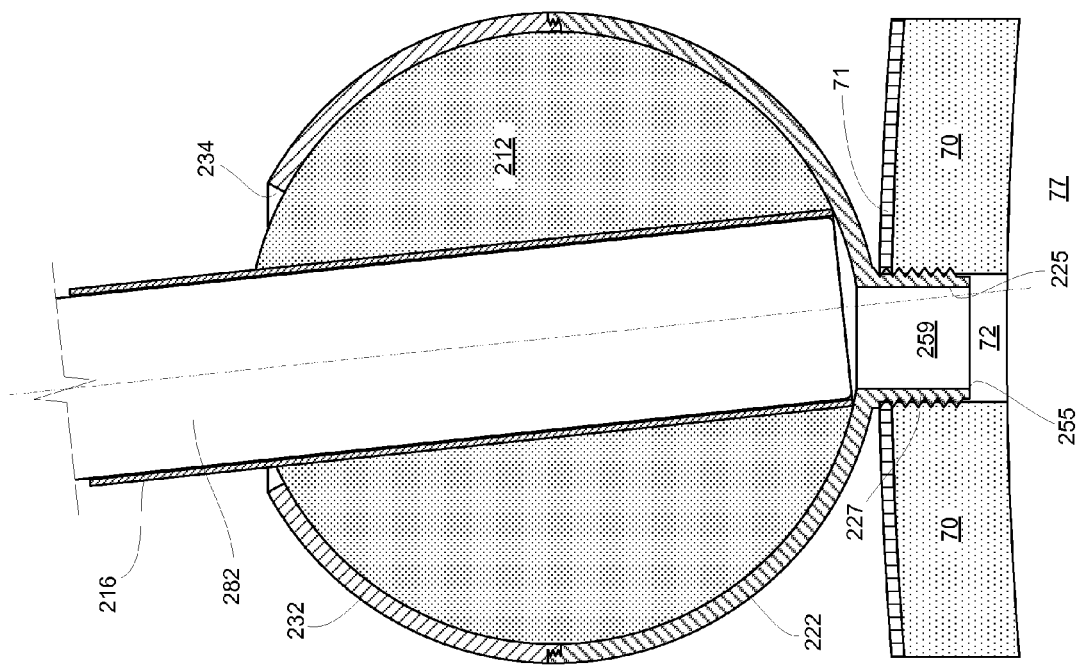

METHOD AND APPARATUS FOR DIRECTED DEVICE PLACEMENT IN THE CEREBRAL VENTRICLES OR OTHER INTRACRANIAL TARGETS

CROSS-REFERENCE TO RELATED APPLICATIONS

This application is a Divisional of and claims the benefit of U.S. patent application Ser. No. 12/479,255, by Alexander C. Flint, titled "Method and apparatus for directed device placement in the cerebral ventricles or other intracranial targets", which was filed Jun. 5, 2009, and which claimed the benefit of Alexander Calhoun Flint U.S. Provisional Application No. 61/059,371, titled "Catheterization of the cerebral ventricles by an ultrasound-aligned guidance system", which was filed Jun. 6, 2008. Each of the said applications is incorporated herein by reference.

BACKGROUND

1. Field of the Invention

This invention relates to intracranial access. Generally, this invention relates to using imagery to establish a trajectory and distance for introduction of a device to a site in the brain and, more particularly, to directed placement of a device to the cerebral ventricles.

2. Description of Related Art

Features in and around the brain (the intracranial contents) may be accessed for diagnosis or treatment by way of a hole drilled through the skull. Accessing the intracranial contents may include introducing a device, such as a catheter or needle, through the hole to a particular site.

It may be necessary to place the device with some degree of accuracy. Particularly, where it is desired to place the tip of a device such as a catheter or a cerebrospinal fluid shunt or a needle into a cerebral ventricle, accurate placement of the tip of the device is necessary.

Accurate intracranial placement of devices is challenging. Conventionally, the placement at the desired position (the target) may be approximated by making the hole in the skull at one of the known landmark locations on the skull, and then introducing the device through the hole in a direction and to a depth that the surgeon estimates will locate the device tip at the target. Stated another way, the conventional approach, representing a current standard of practice, is essentially "blind", entailing some degree of guesswork, and as a result the placement is not always satisfactorily accurate. Misplaced devices may be ineffective, and may result in harm to the patient. Accordingly, it may be necessary to remove and reintroduce an inaccurately placed device one or more additional times, until placement is deemed satisfactory. Repeated placement efforts increase risks of injury or trauma to the patient, such as bleeding or damage to brain tissue or infection.

Ventricular catheters and ventricular shunts are typically left in place for some time following emplacement, with the distal tip at the target and the proximal end outside the cranium. A ventricular catheter may serve as a drain, for example, to control flow of fluid from the ventricles; or, a catheter may serve as a conduit for introduction of a diagnostic or therapeutic substance to the target. The proximal end of the catheter may be connected to a reservoir, from which fluid (such as cerebrospinal fluid) may be removed or into which a therapeutic or diagnostic substance may be introduced. It is preferred to limit movement or play in the location of the device at the hole, to prevent displacement from the target after placement. Accordingly, where the device is to be left in place, it is desirable to employ a small hole in the skull, and typically the hole in the skull for a device that is left in place for some time has a diameter only a few millimeters larger than the diameter of the device.

Various stereotactic guidance systems have been proposed to improve targeting of intracranial sites; these generally must be deployed in an operating theater.

In one approach to directed placement of a catheter, the catheter itself is provided with ultrasound capability. Schultz-Stubner U.S. Patent Publication No. 2007/0083100, for example, describes an ultrasound probe associated with the distal end of a ventriculostomy catheter, operable to provide ultrasound imaging during advancement of the catheter or when the catheter is positioned at a desired location in a cerebral ventricle. Gilbert U.S. Pat. No. 5,690,117 describes an intracranial catheter having a stylet provided with fiberoptics and an ultrasound transducer. Ultrasound probes typically produce a beam that is the same size as the probe cross section, or only slightly larger, and the miniaturized ultrasound probes in these devices are too small to provide an interpretable image that would be deep enough and broad enough to visualize a target and distinguish it from surrounding tissues. Moreover, the imaging parts of these devices are very costly, and the devices are not likely to be reusable, so they are too expensive to be accepted.

Boner et al. U.S. Pat. No. 4,681,103 describes a stereotactic guide for obtaining needle biopsies from the brain. It includes a mounting assembly that is screwed into a burr hole in the patient's skull, and a swivel ball disposed in the assembly, and a locking ring disposed over the swivel ball, which can be reversibly tightened to fix the swivel ball in place or loosened to allow it to swivel. The swivel ball constitutes a socket that receives an intraoperative ultrasound probe, which can be removed and replaced with a needle guide. The "probe is as close to the brain as possible", and is shown as projecting into the hole until it is at or below the level of the dura (that is, at or below the inner table of the skull). Accordingly, the burr hole must be vary large, to accommodate these features. The biopsy needle is inserted through the needle guide, the biopsy is taken, and the needle is removed.

SUMMARY

Generally, in various embodiments, apparatus for directed cranial access to a site includes a guidepiece and a receptacle. The receptacle includes a lower part and an upper part. The lower receptacle part has a rim and a base, and a hollow stem at the base adapted to be mounted in a hole in the skull. The upper receptacle part has a rim and an opening at the top. Each part of the receptacle has an interior spherical surface, and the parts can be joined at the rims to form an inner surface enclosing a generally spherical interior. The guidepiece includes a body having a spherical outer surface and a lumen through the center, defining an alignment axis. The guidepiece may further include a bore through the center thereof, and a guide tube in the bore, and in such embodiments the lumen of the guide tube constitutes the guidepiece lumen. Where a guide tube is present, it may project away from, or may end flush with, the guidepiece body surface. The guidepiece is dimensioned to fit rotatably within the receptacle interior, and the apparatus is assembled by joining the receptacle over the guidepiece body, so that the insertion end of the guidepiece lumen is situated at the top opening; or, where a guide tube is present and projects from the guidepiece body, so that the insertion end of the guide tube projects through the top opening. The guidepiece lumen (or, where a guide tube is present, the guide tube lumen) is dimensioned to accept an imaging device such as an ultrasound probe during an imaging stage; and to accept an adaptor is provided, dimensioned to accept a device to be placed at the site during a placement stage. An optimum trajectory to the site is established by inserting the probe into the guidepiece (guide tube) lumen to present an image, swiveling the guidepiece until the image shows that the alignment axis is aligned along an optimal trajectory to the site, and tightening the receptacle to lock the guidepiece and establish the trajectory. The distance along the trajectory to the site is determined with reference to the image. The probe is withdrawn from the guidepiece (guide tube) lumen and the adaptor is inserted into the guidepiece (guide tube) lumen, and the device is inserted through the adaptor over the determined distance along the established trajectory to the site. Thereafter the apparatus can be withdrawn, leaving the device at the site.

Accordingly, in embodiments of one general aspect the invention features apparatus for directed cranial access to a site, including a guidepiece and a receptacle; the receptacle includes a lower part and an upper part, the lower receptacle part having a rim and a base and a hollow stem at the base adapted to be mounted in a hole in the skull, and the upper receptacle part having a rim and an opening at the top, each part of the receptacle having an interior spherical surface, and the upper and lower receptacle parts can be joined at the rims to form an inner surface enclosing a generally spherical interior; and the guidepiece includes a body having a spherical outer surface and a lumen through the center, defining an alignment axis; the guidepiece is dimensioned to fit rotatably within the receptacle interior, and the apparatus is assembled by joining the receptacle parts over the guidepiece body, with the alignment axis projecting from the insertion end of the guidepiece lumen through the top opening; the guidepiece lumen is configured and dimensioned to accept an imaging device.

A "spherical" surface, as that term is employed herein, means and includes a surface that constitutes part of a sphere; and a "spherical" surface, as that term is used herein, further includes an interrupted surface.

In some embodiments the guidepiece body further includes a bore through the center thereof, and a guide tube in the bore, wherein a lumen in the guide tube constitutes the guidepiece lumen.

In some embodiments the apparatus further includes an adaptor insertable within the guide tube including an adaptor bore configured and dimensioned to accept a device to be placed at the site. In some such embodiments the axis defined by the adaptor bore coincides with the alignment axis of the guidepiece; the adaptor bore may be cylindrical, having a diameter about the same as, or slightly larger than the diameter of the device to be placed at the site.

In embodiments of another general aspect the invention features a method for placing a device at an intracranial site, by: forming a hole in the skull; assembling the apparatus as described above and mounting the apparatus in the skull; inserting an imaging device into the guidepiece (guide tube) lumen and activating imaging apparatus associated with the imaging device to generate an image of the intracranial contents; swiveling the guidepiece until the image shows that the alignment axis is aligned along an optimal trajectory to the site, and tightening the receptacle to lock the guidepiece and establish the trajectory; determining the distance along the trajectory to the site with reference to the image; withdrawing the probe from the guidepiece (guide tube) lumen; inserting an adaptor as described above into the guidepiece (guide tube) lumen; inserting the device through the adaptor bore over the determined distance along the established trajectory to the site; and withdrawing the apparatus, leaving the device in place at the site.

In some embodiments the device is marked with depth indicia to aid in inserting the device over the determined distance to the target. In some embodiments, for example, a mark may be located at a point that is aligned with the insertion end of the adaptor when the device tip is at the position where the end of the probe had been; an accurate insertion distance can be measured in a proximal direction along the device, and the device is inserted to that point. In some embodiments, for example, marks may be located at intervals along the device length. In some embodiments these marking approaches may be combined.

The invention provides for improved patient safety in intracranial device placement, by improving the accuracy of device placement and by reducing or eliminating the necessity to make repeated placement attempts. Risks associated with conventional "blind" approaches, or approaches requiring estimation or guess work, are mitigated.

The invention provides for orienting an imaging device (such as an ultrasound probe) on an alignment axis along an optimal placement trajectory to toward an intracranial target, and for determination of a device insertion distance; for fixing the alignment axis; and for inserting a device across the fixed alignment axis over the determined distance to the target.

According to some aspects of the invention the hole in the skull has a diameter suitable for placement of devices that are to be left in place, and can be made using a twist drill, for example, not requiring electrical power. The procedure can be conducted outside the operating theater. Moreover, the small hole is of a diameter suitable for placement of a device (such as a catheter or the like) that is to be left in place for an extended time (typical of a ventriculostomy, for example).

The invention provides for directed placement of devices to intracranial targets that are not readily accessible using a conventional blind approach. For example, devices (such as catheters, for example) may be accurately placed in specified parts of the ventricular system (such as, for example, the temporal horn of the lateral ventricle) or other intracranial targets. Because according to the invention the device insertion trajectory can be at an angle with respect to the axis of the hole in the skull (that is, the trajectory can be significantly off the axis of the hole in the skull), it is not necessary that the hole be located at a point overlying the target; as a result, a trajectory to the target that avoids critical brain tissues can be established.

The guidepiece according to some embodiments of the invention can be employed with any imaging device having any of a range of shapes and sizes, to locate an optimal insertion trajectory to an intracranial target, and can be locked in place to establish the insertion trajectory to the target; and then, by use of an adaptor where necessary, the same guidepiece, locked in place, can be employed to insert any of a variety of devices, having any of a range of shapes and sizes, along the same trajectory to the target.

Following directed placement of a device to the target, the apparatus can be removed, leaving the device in place substantially undisturbed.

The method of the invention employs many tools familiar to practitioners (standard drill and bit, catheter or other device, etc.), and can be readily adapted to current practice with very small modification and an easy learning curve.

BRIEF DESCRIPTION OF THE DRAWINGS

FIG. 1A is a diagrammatic sketch in an elevational view showing a guidepiece according to an embodiment of the invention.

FIG. 1B is a diagrammatic sketch showing a guidepiece according to an embodiment of the invention, in a sectional view in an equatorial plane (as indicated at B-B in FIG. 1A).

FIG. 2 is a diagrammatic sketch showing a lower (cup) part of a guidepiece receptacle according to an embodiment of the invention, in an elevational view.

FIG. 3 is a diagrammatic sketch showing an upper (cover) part of a guidepiece receptacle according to an embodiment of the invention, in an elevational view.

FIGS. 5A, 5B, 5C are diagrammatic sketches illustrating various orientations of a guidepiece in a receptacle according to an embodiment of the invention, in a sectional view thru an alignment axis.

FIGS. 6A, 6B, 6C are diagrammatic sketches illustrating various orientations of a guidepiece in a receptacle according to an embodiment of the invention, in a plan view.

FIGS. 7A-7D are diagrammatic sketches in sectional view showing stages in mounting cranial access apparatus according to an embodiment of the invention.

FIGS. 8A and 8B are diagrammatic sketches in sectional view showing deployment and operation of an ultrasound imaging device in cranial access apparatus according to an embodiment of the invention.

FIG. 9 is a diagrammatic sketch showing display of an image obtained by operation of an ultrasound imaging device as shown in FIG. 8B.

FIGS. 10A, 10B, 11A, 11B, 12A, 12B are diagrammatic sketches showing guidepiece adaptors according to examples of embodiments of the invention. FIGS. 10A, 11A, 12A are in three-dimensional view and FIGS. 10B, 11B, 12B are in sectional view as indicated at B-B thru FIGS. 10A, 11A, 12A, respectively.

FIG. 13 is a diagrammatic sketch in three-dimensional view showing cranial access apparatus, according to an embodiment of the invention.

FIGS. 14A-14E are diagrammatic sketches in sectional view showing deployment of an intracranial catheter using cranial access apparatus, according to an embodiment of the invention.

FIGS. 16A, 16B, 17A, 17B are diagrammatic sketches showing various guidepiece adaptor configurations according to examples of embodiments of the invention. FIGS. 16A, 17A are in three-dimensional view and FIGS. 16B, 17B, are in sectional view as indicated at B-B thru FIGS. 16A, 17A, respectively.

FIG. 18 is a diagrammatic sketch in three-dimensional view showing cranial access apparatus, according to an embodiment of the invention.

FIGS. 19A, 20A, 21A are in three-dimensional view and FIGS. 19B, 20B, 21B are in sectional view in an equatorial plane as indicated at B-B thru FIGS. 19A, 20A, 21A, respectively.

FIG. 22A is a diagrammatic sketch in a sectional view showing cranial access apparatus according to another embodiment of the invention.

FIG. 22B is a diagrammatic sketch showing display of an image obtained by operation of an ultrasound imaging device as shown in FIG. 22A.

DETAILED DESCRIPTION

Figure 4A:
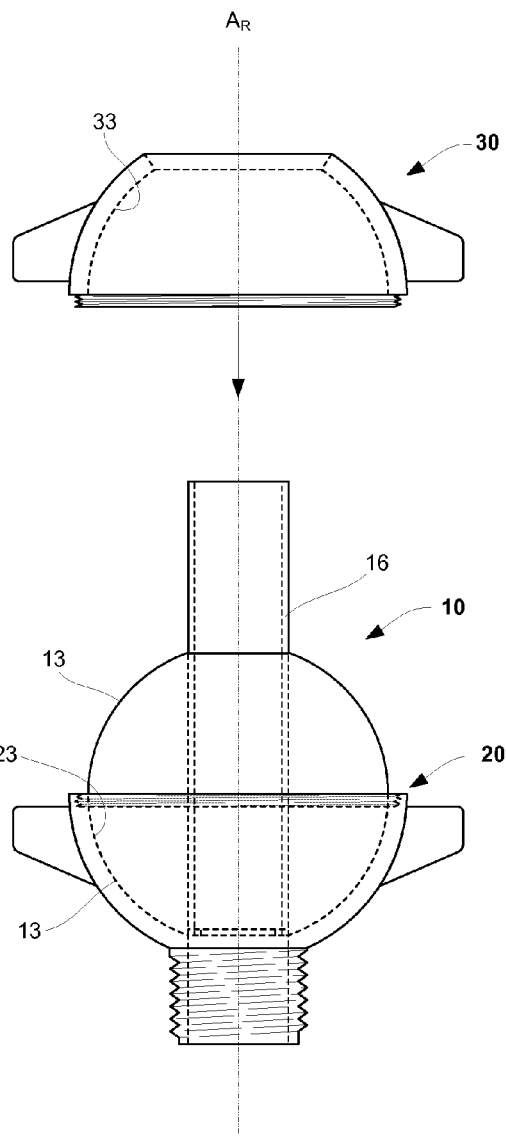
FIGS. 4A and 4B are diagrammatic sketches showing stages in assembling cranial access apparatus according to an embodiment of the invention, in an elevational view.

The invention will now be described in further detail by reference to the drawings, which illustrate alternative embodiments of the invention. The drawings are diagrammatic, showing features of the invention and their relation to other features and structures, and are not made to scale. For improved clarity of presentation, in the FIGs. illustrating embodiments of the invention, features corresponding to features shown in other drawings are not all particularly renumbered, although they are all readily identifiable in all the FIGs.

In various embodiments, cranial access apparatus includes a guidepiece mounted in a receptacle. The receptacle includes a lower part (cup) and an upper part (cover). The guidepiece includes a body having the form of a ball having a bore through the center, and a guide tube in the bore. In some embodiments the guide tube projects from the body, constituting a receiving end of the guidepiece. The parts of the receptacle are configured so that when the apparatus is assembled their inner surfaces conform generally to the surface of the guidepiece body. The base of the receptacle cup has a port that opens through a hollow stem. The receptacle stem is configured and dimensioned for insertion into a hole in the skull of the subject being treated. The cover has an opening at the top, to accommodate the projecting guide tube at the receiving end of the guidepiece when the apparatus is assembled.

An embodiment of a guidepiece is shown at 10 in FIGS. 1A and 1B. The guidepiece body is a ball 12, that is, it has a generally spherical outer surface 13. A cylindrical bore through the center of the ball defines a cylindrical inner surface 11 and an alignment axis A. A guide tube 16 in the bore has an outer surface 17 and an inner surface 15 defining a guide tube lumen 19. In the embodiment shown here a portion of the guide tube projects from the guidepiece body, constituting a receiving end into which a device can be deployed, as indicated by arrow 18. In the embodiment shown here the end of the guidepiece tube opposite the receiving end is generally flush with the body surface. The guidepiece may be constructed of any of a variety of materials, including plastics, metals, and ceramics, for example, and may include combinations of materials, and suitable materials may preferably be sterilizable. For instance, the guidepiece may be formed substantially of one selected material, coated or plated with another selected material. The guidepiece body and tube may be made of the same or of different materials. The guidepiece body and tube may be formed in a single piece, for example by casting or molding. Or, alternatively, the tube and body may be made as separate parts, and the guidepiece may be assembled by inserting the tube into the bore in the body; the tube may be affixed in the body using an adhesive, for example, or the tube may be press-fitted in the body.

Embodiments of receptacle parts configured and dimensioned to receive the guidepiece of FIGS. 1A and 1B are shown in FIGS. 2 (lower, cup part) and 3 (upper, cover part). Referring to FIG. 2, the lower part 20 in this embodiment has the form generally of a cup 22 having a rim 35 and a base and having a hollow stem 27 at the base. An inner surface 23 of the cup 22 is generally spherical, enclosing an interior 29 that has a diameter about the same as the diameter of the corresponding guidepiece body. The inner surface 25 of the stem 27 defines a receptacle axis $A_R$ and encloses a stem lumen that communicates through a port at the base of the cup with the interior 29. The outer surface of the stem is at least partly threaded, as indicated at 26. The rim 35 of the cup is situated in a plane generally perpendicular to the receptacle axis $A_R$, which runs through the geometric center of the spherical cup surface 23 and through the geometric axis of the stem lumen. Referring now to FIG. 3, the upper part 30 in this embodiment has the form generally of a cover 32 having a rim 37, and an opening 34 at the top. An inner surface 33 of the cover 32 is generally spherical, enclosing an interior 39 that has a diameter about the same as the diameter of the corresponding guidepiece body. The rim 37 of the cover is situated in a plane generally perpendicular to the receptacle axis $A_R$, which runs through the geometric center of the spherical cover surface 33 and through the center of the opening 34. The rims 35, 37 are threaded complementarily so that the cover and the cup can be screwed together; in the example shown the cover has "male" threading and the cup has "female" threading. In the example shown the lower receptacle part 20 and the upper receptacle part 30 are provided with "wings" 34, 34' and 36, 36' to aid the user in manually turning the cup stem into a hole in the subject's skull, and to aid the user in manually turning the cup and cover in relation to one another, about the receptacle axis $A_R$. The receptacle may be constructed of any of a variety of materials, including plastics, metals, and ceramics, for example, and may include combinations of materials. For instance, parts of the receptacle may variously be formed substantially of one selected material, coated or plated with another selected material. The upper and lower parts of the receptacle may be made of the same or of different materials; and the stem and cup of the lower part may be made of the same or of different materials, and suitable materials may preferably be sterilizable. The stem and cup of the lower part may be formed in a single piece, for example by casting or molding. Or, alternatively, the stem and cup of the lower part may be made as separate parts, and the lower part may be assembled by inserting an end of the stem into an opening in the cup; the stem may be affixed in the cup using an adhesive, for example, or the stem may be press-fitted in the body, for example. The threaded portion of the stem should be of a sufficiently hard material, and the threads should be sufficiently sharp, so that the stem self-taps into the hole in the skull. Accordingly, any of a variety of metals or high temperature ceramics may be particularly suitable, but any of a variety of suitably hard plastics may also be suitable.

Generally, the respective surfaces of the receptacle and of the guidepiece body are configured to provide for rotation of the guidepiece body within the receptacle, generally about the geometric center of the guidepiece body. Accordingly the diameter of the outer surface of the guidepiece body is preferably about the same as, or less (by a narrow tolerance) than, the diameter of the inner surface of the receptacle. Generally, for example, the outer diameter of the ball can be the same as the inner diameter of the fully assembled and fully screwed together upper and lower receptacle parts, so that as the upper and lower pieces are screwed together, the ball is locked in place before the parts are fully screwed together. The inner surface of one or both of the receptacle parts and/or the outer surface of the guidepiece body may be more or less smooth or, alternatively, the outer surface of the ball and/or the inner surface of one or both of the upper and lower parts can be made finely bumped, ridged, or frosted to increase the coefficient of friction between the surfaces.

A "spherical" surface, as that term is employed herein, means and includes a surface that constitutes part of a sphere. For example in the embodiments shown in the drawings the guidepiece body constitutes a ball intersected by a cylinder whose axis passes through the center of the ball. The intersection of the cylinder and the ball describes two circles describing two spherical caps and, accordingly, the "spherical" outer surface of the guidepiece body constitutes a sphere lacking spherical caps at opposite poles. Similarly, for example, in the embodiments shown in the drawings the "spherical" inner surface of each receptacle part constitutes a part of a sphere formed by intersecting a sphere by two parallel planes, one near the equator (defining a rim) and the other near a pole (defining an opening to the stem lumen in the lower receptacle part; defining the opening at the top in the upper receptacle part).

In the examples shown in the FIGs the surfaces are shown as being continuous within the boundaries described by the intersecting planes. A "spherical" surface, as that term is used herein, need not be continuous, and the term further includes an interrupted surface. For example, the "spherical" outer surface of the guidepiece body may constitute a part of a sphere that may be interrupted by grooves or dimples or other features in the outer portion of the ball. And, for example, the "spherical" inner surface of either (or both) the receptacle parts may constitute a part of a sphere that may be interrupted by grooves or dimples or other features in the inner wall.

A suitable guidepiece body diameter can be within a broad range. The body must be sufficiently large to accommodate a probe within the guide tube. The guidepiece rotates (swivels) about the spherical center of the guidepiece body and, as may be appreciated by inspection of the drawings, a greater viewing range may be obtained if the center of the guidepiece body is as close as is practicable to the outer table of the skull. That is, it may be desirable for the guidepiece body (and the corresponding receptacle surfaces) to have a smaller diameter. As discussed below, the inner diameter of the stem (and, accordingly, the diameter of the drill hole in the skull) may according to the invention be kept small as the size of the guidepiece body and receptacle cup and cover are made larger.

In the embodiments shown in the FIGs., the walls of the cup and the cover are generally uniformly thick, so that the outer surface of the cover and cup are generally spherical. The outer surfaces may have other shapes. For example, the outer surfaces may have a generally polygonal (for example, hexagonal) shape in a transverse sectional view. In such embodiments the user may be able to grip the cup and cover securely enough so that the "wings" are not required, and may be omitted. Similarly, any irregularity in the outer surfaces of the cup and cover (for example, ribs or knurling) may provide for a secure grip and, in this respect the "wings" may be described as a form of irregularity in the outer surfaces of the cup and cover, respectively.

Figure 4B:
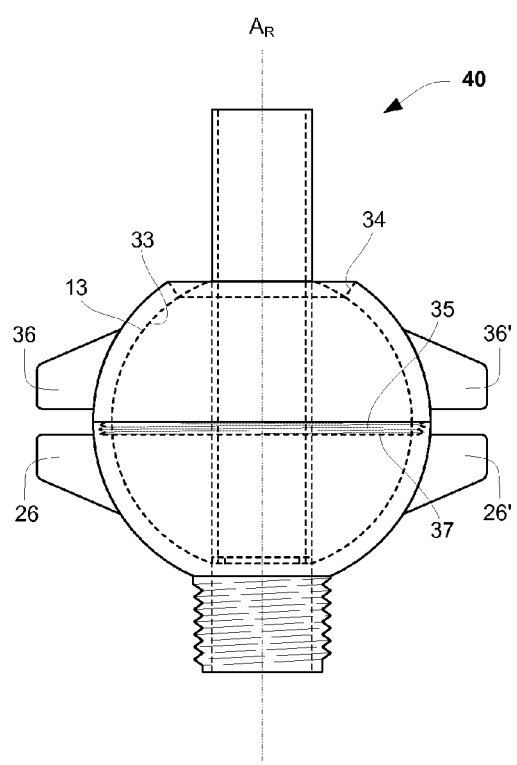

Assembly of the cranial access apparatus is illustrated, in sectional views along the receptacle axis, in two stages at FIGS. 4A and 4B. The guidepiece 10 is nested into the cup 20 with the projecting part of the guide tube 16 directed generally away from the cup, as shown in FIG. 4A. Because the spherical surface 13 of the guidepiece body has a diameter approximately the same as (or slightly less than) the diameter of the spherical inner surface 23 of the cup 20, the guidepiece can swivel about its geometric center within the cup. The cover and the cup are aligned along the receptacle axis $A_R$ and the cover and cup are moved toward one another (as suggested by the arrow) so that their respective threaded rims 37, 35 meet, and the projecting part of the guide tube 16 passes through the opening 34 in the cover. Once the threads engage, the cup and cover are screwed together by rotating them to one another about the receptacle axis $A_R$ to mate the threads. (The "wings" 36, 36' are shown in the FIGs. as being aligned with the "wings" 34, 34'; they will of course move out of alignment as the cover and cup are screwed together.) As the mating proceeds, geometric centers of the spherical inner surfaces 33, 23 approach one another and eventually coincide. As noted above, in some embodiments the spherical surface 13 of the guidepiece body may have a diameter approximately the same as the diameter of the spherical inner surfaces 33, 23 of the cup 30 and cover 20, and in other embodiments the spherical surface 13 of the guidepiece body may have a diameter slightly less than the diameter of the spherical inner surfaces of the cup 30 and cover 20.

In embodiments in which the spherical surface 13 of the guidepiece body has a diameter the same as the diameter of the spherical inner surfaces 33, 23 of the cup 30 and cover 20, when the spherical centers coincide the contact of the receptacle and the guidepiece body can inhibit movement of the guidepiece swivel about its geometric center within the cup. On the other hand, in embodiments in which the spherical surface 13 of the guidepiece body has a diameter slightly less than the diameter of the spherical inner surface 33 of the cup 30, the guidepiece can when the spherical centers coincide swivel about its geometric center within the cup. The respective rims of the cover and cup can be dimensioned so that they may be advanced further together (that is, for example, the threads may not be turned to their limit when the spherical centers of the receptacle parts coincide), so that even in embodiments where the guidepiece body diameter is smaller than the diameters of the inner surfaces of the receptacle parts, the receptacle can be tightened so that the parts press inwardly against the guidepiece body and inhibit the guidepiece form swiveling. A resulting assembly is shown at 40 in FIG. 4B.

As noted above, where the geometric centers of the cup and the cover are both aligned with the geometric center of the guidepiece body, the guidepiece body can swivel (tilt and rotate) about a center of rotation as shown in FIGS. 5A, 5B, 5C and 6A, 6B, 6C. For reference, in each of FIGS. 5A, 5B, 5C the receptacle axis is in the plane of the drawing and oriented vertically on the page; and in each of FIGS. 6A, 6B, 6C the receptacle axis is oriented perpendicularly to the plane of the drawing. In FIG. 5B the guidepiece alignment axis A is aligned with the receptacle axis. In each of FIGS. 5A and 5C the guidepiece is tilted so that its alignment axis (respectively, A', A'') is unaligned with the receptacle axis. In each of FIGS. 6A, 6B, 6C the guidepiece has been tilted in a selected direction away from the receptacle axis. The extent to which the guidepiece may be tilted is as a practical matter limited by the shape and dimensions of the opening 34, inasmuch as the projecting portion of the alignment tube 16 may impinge with the edge of the opening 34. Resistance to swiveling or rotational movement of the guidepiece within the receptacle can be increased or decreased by turning the cover in relation to the cup to tighten or loosen the inward force exerted by the cup and cover on the guidepiece body. At some stages during use of the apparatus, it is desirable to tighten the receptacle so that the guidepiece is immobile under the conditions of use. At other stages it is desirable to loosen the receptacle enough to allow the user to tilt or rotate the guidepiece within the receptacle to direct or redirect the alignment axis in relation to features within the skull. The resistance may be finely adjusted to permit rotation and tilt of the guidepiece and yet prevent undesired movements. Portions of the inner surfaces of the receptacle and/or of the guidepiece body may optionally be textured to augment the frictional resistance to movement of the guidepiece.

FIGS. 7A, 7B, 7C, 7D show, in sectional view, stages in a procedure for reversibly installing the cranial access apparatus into the skull of a subject to be treated. A portion 70 of the skull is shown overlain by the skin 71; and underlain by the intracranial contents 77 in these FIGs.

In one stage, a hole is created in the skull, as shown at 72 in FIG. 7A. In practice, this entails the following:

Using standard neurosurgical techniques, an incision is made at the appropriate location in the subject's skull. For example, in a transfrontal approach to accessing a cerebral ventricle an incision is made near a location on the skull known as Kocher's point.

Thereafter, using standard neurosurgical techniques, a drill hole is made using a hand drill or other device with a drill bit size suitable to form a hole having an inside diameter D minimally larger than the outer diameter of a device that is to be advanced into the target (for example, the cerebral ventricle). Preferably the hole diameter is large enough to allow for some angular displacement of the particular device that is to be deployed through the hole. For an indwelling cerebral catheter such as a ventricular drain or ventricular shunt, for example, a standard hole may have a diameter in a range about 6-8 mm. A drill bit having a ¼ inch (6.4 mm) size and as large as about ½ inch (12.5 mm) size may be suitable, for example. The diameter of the drill hole should be at least a great as the diameter of the device to be inserted through it; for a 6 French catheter, having a nominal 3 mm diameter, a drill hole as small as about 5 mm may be suitable.

Thereafter, using standard neurosurgical techniques, the dura mater is incised. Following incision of the dura mater, if ultrasound imaging is to be employed, a small amount of a sterile, preservative-free ultrasound gel is disposed within the drill hole to allow for clear insonation. An isotonic saline solution may be employed, but over time the saline may disperse from the drill hole; and a gel can effectively serve as a matrix to support the saline in the desired region. An example of a suitable such gel is an ultrasound gel marketed by Sonotech, Inc. under the name "UltraBio Sterile".

In a subsequent stage, the cranial access apparatus 40 is installed in the hole in the skull, with a result as shown in FIG. 7D. Where the apparatus is assembled prior to installation in the skull, this entails the following:

The assembly 40 is screwed into the hole 72, using the lower "wings" 34, 34' to rotate the assembly in a first direction (e.g., clockwise) to advance the threads on the stem of the cup into the hole 72. The apparatus is screwed into the hole to an extent sufficient to firmly anchor it to the skull, while permitting eventual removal of the apparatus by rotating it the opposite way (e.g., counter-clockwise). It may be desirable, prior to installation of the apparatus into the skull, to screw the cover and the cap together tightly enough to inhibit movement of the guidepiece and thereby stabilize the assembly.

As FIG. 7D shows, the apparatus provides direct access through the alignment tube lumen 19 and the stem lumen 59 and the inner portion of the hole 72 to features in the intracranial contents 77.

In other embodiments the cranial access apparatus may be assembled in situ, by stages illustrated in FIGS. 7B, 7C, 7D.

In a stage shown in FIG. 7B, the lower (cup) part 20 of the receptacle is screwed into the hole 72, using the lower "wings" 34, 34' to rotate the assembly in a first direction (e.g., clockwise) to advance the threads on the stem of the cup into the hole 72. Either at this stage or later the apparatus is screwed into the hole to an extent sufficient to firmly anchor it to the skull, while permitting eventual removal of the apparatus by rotating it the opposite way (e.g., counter-clockwise).

In a subsequent stage shown in FIG. 7C, the guidepiece 10 is nested into the cup 20 with the projecting part of the guide tube 16 directed generally away from the cup.

Thereafter, the cover is aligned with the cup along the receptacle axis, and the cover is screwed onto the cup, generally as described above with reference to FIGS. 4A, 4B, with a result as shown in FIG. 7D.

With either method of assembly, when ultrasound imaging is desired, sufficient sterile, preservative-free ultrasound gel is applied to the receptacle stem and lower aspect of the guidepiece to provide adequate ultrasound insonation.

The outer diameter of the receptacle stem is matched to the hole diameter. For example, where the hole is made using a ¼ inch diameter drill bit, the receptacle stem is dimensioned so that the threaded portion is self-tapping when turned into the hole, resulting in a secure mount of the apparatus in the hole.

Once the cranial access apparatus has been installed onto the skull of the subject to be treated, the apparatus can receive any of a variety of devices, for imaging or diagnosis or treatment, for example.

In some procedures, accurate placement of a device (such as, for example, an intracranial catheter or similar device) in a particular site may be required. For example, it is desirable to accurately place a catheter or similar device. Accordingly, in some embodiments cranial access apparatus is installed, and an imaging device is inserted in the guide tube to visualize features in the underlying intracranial contents. The guidepiece is then swiveled to bring the alignment axis along a path that the imaging device shows to be optimal to access a particular treatment site. The cover and cup may thereafter be tightened so that the guidepiece does not swivel, that is, to secure the orientation of the guidepiece alignment axis along the optimal path, and the imaging device is withdrawn. Thereafter a device for accessing the particular site is introduced through the secured guidepiece to the treatment site.

FIGS. 8A and 8B show stages in insertion and use of an imaging device (in this instance, an ultrasound imaging probe) in the guidepiece of cranial access apparatus 40 that has been installed onto the skull. The probe is inserted into the receiving end of the guidepiece. The probe 80 includes a probe body 82 electrically connected by a cable 81 to ultrasound imaging apparatus (not shown in the FIGs.). The inner surface of the guide tube is configured and generally dimensioned to accommodate the shape and size of the imaging device. In the example shown here, for example, the probe may be generally cylindrical and, accordingly, the guide tube inner surface is generally cylindrical; and the inside diameter of the tube is slightly larger than the outer diameter of the probe. Other configurations are contemplated, as discussed below with reference, for example, to FIGS. 16A, 16B, 17A, 17B, 23A.

In one stage, the probe is inserted into the guidepiece tube. In practice, this entails the following:

The probe is sheathed in a standard sterile covering and brought into the sterile surgical field.

The sheathed probe is inserted into the receiving end of the guidepiece 40 and is advanced through the guide tube until the tip of the probe rests at the foot of the tube. Referring to FIGS. 1A, 1B, a retaining ring 14 at the foot of the tube may provide a mechanical stop for advancement of the probe into the tube.

The selected probe may have a width (or diameter) larger than the diameter of the bore through the receptacle stem, and the guide tube is dimensioned accordingly, as is discussed below with reference to FIG. 19A, for example. Any of a variety of ultrasound probes may be used, and probes identified as being for pediatric or neonatal use may be preferred. Suitable probes have an image width and scan depth sufficient to adequately provide location of the site of interest; for instance the surface of the lateral ventricle is typically about 5 cm below the outer table of the skull in an adult. Examples include ultrasound transducers marketed as the "M-series" by SonoSite, Inc., Bothell, Wash., such as for example the model "P10x", having a 10 mm wide linear image and a 14 cm scan depth, and a larger probe housing width about 12-14 mm. Larger probes can be accommodated within the guidepiece by providing suitably wide guidetube inner dimensions.

In a subsequent stage, the site is visualized and the optimal trajectory and distance to the site is determined. In practice, this entails the following:

The guidepiece receptacle cover is rotated about the receptacle axis in relation to the guidepiece receptacle cup to tighten or loosen the force on the guidepiece body, to allow the guidepiece to swivel. The imaging apparatus is started, and the guidepiece, carrying the probe, is tilted until the general region of the brain near the site to be accessed is visualized. Where for example the procedure is placement of a catheter into the lateral ventricle, the guidepiece is tilted so that the interface of the brain and the cerebrospinal fluid of the lateral ventricle is sonographically visualized. FIG. 8B shows an example of an imaging procedure, in which an imaging signal 84 projects along the alignment axis A toward the target 88 within the intracranial contents. (In the stage shown here, the alignment axis of the guidepiece is coincident with the receptacle axis.) The corresponding image appears on a display, as shown for example in FIG. 9.

Thereafter the probe is rotated within the guidepiece tube, or the guidepiece tube is rotated about the alignment axis, until the sonographic plane is approximately coronal, and then the guidepiece, carrying the probe, is swiveled until the sonographic image shows that the alignment axis is generally centered on the lateral ventricle.

Additional information can optionally be obtained by rotating the probe within the guidepiece tube, or rotating the guidepiece tube about the alignment axis, until the sonographic plane is approximately sagittal, or is intermediate between coronal and sagittal.

When the optimal trajectory to the center of the lateral ventricle is identified sonographically, the receptacle is tightened (by tightening the cover on the cup) to immobilize the guidepiece within the receptacle, thereby locking the alignment axis A coincident with the optimal trajectory.

With the guidepiece immobilized, the probe can be rotated about the alignment axis within the fixed guide tube (to view various sonographic planes) to confirm that the selected trajectory is optimal and, if not, the receptacle can be loosened and the guidepiece can be tilted to improve the alignment.

Once the optimal trajectory has been determined, the distance from the probe tip to the site (in this example, the surface of the lateral ventricle) is measured sonographically along the trajectory (that is, along the alignment axis). Then the imaging device is withdrawn from the guidepiece.

Once the guidepiece has been locked in place within the receptacle so that the alignment axis is coincident with an optimal access trajectory to the site, the apparatus can receive any of a variety of additional devices, depending upon the particular procedure or treatment.

Examples of such devices include ventricular catheters, needles, ventriculoscopes, ventricular shunts (such as ventriculoperitoneal shunts). Such devices may typically have smaller cross-sections than the imaging device (e.g., ultrasound probe) and, accordingly, for introduction of such a device into the guidepiece tube, an adaptor may be provided.

An assortment of guidepiece adaptors, suitable for use in a guidepiece generally as described above, are illustrated by way of example in FIGS. 10A, 10B, 11A, 11B, 12A, 12B. The corresponding guidepiece is shown at 10 in FIG. 13. In these examples the adaptors are configured to fit within the guidepiece tube 16, and to receive devices having a circular cross-section that is slightly less than the inside diameter idt of the guidepiece tube. Accordingly, each of the adaptors 100, 110, 120 has a circular cross-section, with an outside diameter 105, 115, 125 respectively slightly less than the inside diameter idt of the corresponding guidepiece tube 16; and each adaptor has an inner surface 107, 117, 127 defining an axial bore having a diameter ida', ida", ida"', slightly greater than the outside diameter of a device to be introduced through it. The adaptor is introduced into the receiving end of the guidepiece tube 16 and advanced to a stop. Where a stop ring 14 is provided at the foot of the tube, and the adaptor is longer than (or the same length as) the guidepiece tube, the adaptor may rest upon the ring 14 at the foot of the tube. In the examples shown in these FIGs., at one end (a receiving end) of each adaptor tube are tabs 102, 102'; 112, 112'; 122, 122' which project beyond the adaptor wall; where the adaptor is shorter than the guidepiece tube, or where a stop ring 14 is not provided, or to provide a redundant stop function, the tabs may rest upon the receiving end of the tube, preventing further advancement of the adaptor into the guidepiece.

For a given guidepiece a set of adaptors may be provided, all having an outside diameter appropriate to the inside diameter of the guidepiece tube; and each having an axial bore configured and dimensioned to accommodate a variety of particular devices. Many devices have a circular cross-section, for example, and their diameters may be standardized.

FIGS. 14A-14E show stages in deployment of a device (in this instance, a ventricular catheter) in cranial access apparatus 40 that has been installed onto the skull and locked into alignment along an optimal trajectory, generally as described above.

In one stage, the device is inserted into the guidepiece. In practice, this entails the following:

If required, an adaptor is inserted into the guidepiece, as shown in FIG. 14A. Adaptor 110 is configured and dimensioned to fit into the guidepiece tube; that is, where (as here) the guidepiece tube has a cylindrical inner surface 15 the adaptor has a cylindrical outer surface 115. The adaptor additionally is configured and dimensioned to accommodate the particular device to be introduced. Where the device to be introduced has a circular cross-section, adaptor 110 has an inner surface 117 defining an axial bore having a diameter ida slightly greater than the outer diameter of the device. A typical ventricular catheter, for example, may be a "9 French" catheter, having a diameter about 3 mm; and a suitable corresponding bore diameter may be, for example, 3.4-4.0 mm. The difference between the bore diameter and the tubing or device outer diameter for which it is intended is chosen according to specific needs, as greater differences allow for greater ease of passage but also allow for greater degrees of possible error in the angle of approach to the target. For example, for a 5 cm long bore and a 3 mm wide catheter, an inner bore diameter of 3.9 mm would yield a maximum 1 degree error in the angle of approach. For a depth of target of 10.5 cm below the top of the bore, a 1 degree error would lead to the tip of the catheter missing the optimum target by 1.8 mm, which is less than the diameter of the catheter and a very small fraction of the size of typical intracranial targets such as the ventricular system.

As FIG. 14B illustrates, the bore through the adaptor is coaxial along the alignment axis A of the guidepiece. Where appropriate, the catheter or device may be lubricated with a suitable sterile, preservative-free lubricant to facilitate advancement of the catheter or device through the bore.

In a subsequent stage, the device is inserted into the receiving end of the adaptor-fitted apparatus 140, as shown in FIG. 14B. In the example shown here, the device is a ventricular catheter 142 having a perforated tip region 144. The tip 144 of the device is advanced through the adaptor bore to the foot of the guidepiece tube, and then into the intracranial contents 77 and a further distance toward and into the target site 88, as shown in FIG. 14C. The distance to which the tip is advanced is determined by correlation with the distance from the probe tip to the site, as measured during the imaging procedure. To facilitate accurately advancing the device to the desired distance the device may be marked with depth indicia to aid in inserting the device over the determined distance to the target. For example, the device may have a mark at a point that is aligned with the insertion end of the adaptor when the device tip is at the position where the end of the probe had been; this provides an indicium from which to measure proximately along the device the distance to which the device should be advanced. Or, for example, the device may be marked at intervals (e.g., cm intervals) to indicate device length as measured from the tip; and the device is inserted to an indicated length that is the sum of the determined distance to the target plus a known adaptor length. Or, both the foregoing approaches may be employed, providing additional depth accuracy by redundancy. To simplify measuring the advance distance, it may be preferred to dimension the adaptor such that the length of the adaptor bore is a nonfractional multiple of the intervals on the device; for example, if the indicia on the device are at cm intervals, then it may be preferred that the adaptor bore be a nonfractional number of cm in length.

The device may be styletted, as is customary for ventricular drain placement, to maintain stiffness and ensure that the device will proceed to and into the site along the optimal trajectory, as established by the alignment axis A of the guidepiece. Proper positioning of the catheter in the lateral ventricle may be confirmed by withdrawal of a small amount of cerebrospinal fluid.

Figures 14D, 14E:
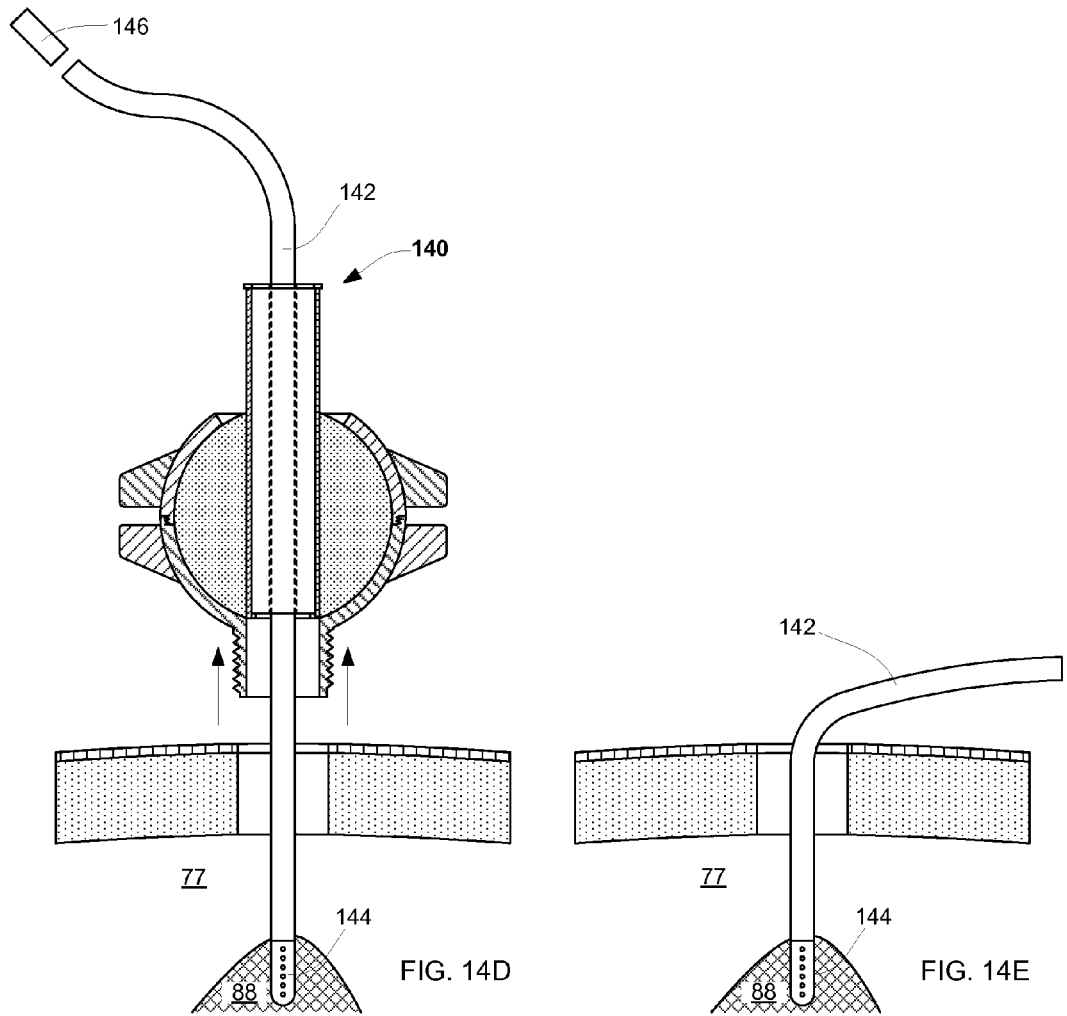

In a subsequent stage, the cranial access apparatus may be removed, while the intracranial device is left in place. In practice, this entails the following:

Where the device is styletted (such as a styletted catheter), the stylet can optionally be withdrawn from the device tubing prior to removing the apparatus. A stopper 146 having an outer diameter no larger than the outer diameter of the catheter or device can be placed on the end of the catheter or device to prevent further outflow of cerebrospinal fluid. The apparatus is disengaged from the skull by grasping the "wings" or other gripping features on the lower (cup) part of the receptacle, and turning the receptacle to unscrew it from the skull. Then the adaptor and the apparatus are withdrawn over the device, as indicated by the arrows in FIG. 14D, with a result as shown in FIG. 14E. The device 142 may be held at the level of the skin or just above the proximal portion of the apparatus 140 during withdrawal of the apparatus, to prevent change in the position of the tip 144 at the site 88. Where the device requires, leakage of fluid outward through the device may be prevented by a stopper 146 at the end of the device opposite the tip. The stopper is narrow enough that it does not interfere with subsequent removal of the adaptor and the apparatus. Removal may be facilitated by withdrawing the adaptor first and thereafter removing the guidepiece and receptacle. Removal may alternatively or additionally facilitated by sequential removal of the upper receptacle part 30 then the guidepiece 10, so that the device (for example, catheter) may be held as close as possible to the skull during the unscrewing and withdrawal of the lower receptacle part 20 (generally following the reverse sequence of stages illustrated in FIGS. 7A-7D.

Alternatively, where the device is styletted, the imaging apparatus may be withdrawn over the device while the stylet is still in place in the device tubing. To permit withdrawal of the adaptor over the styletted device, the proximal end of the stylet must have no transverse dimension greater than the smallest inside dimension (e.g., the inside diameter) of the bore in the adaptor. Leaving the stylet in the device during withdrawal of the apparatus may provide additional control over the device, further ensuring that is does not become displaced from the target.

Figure 15:
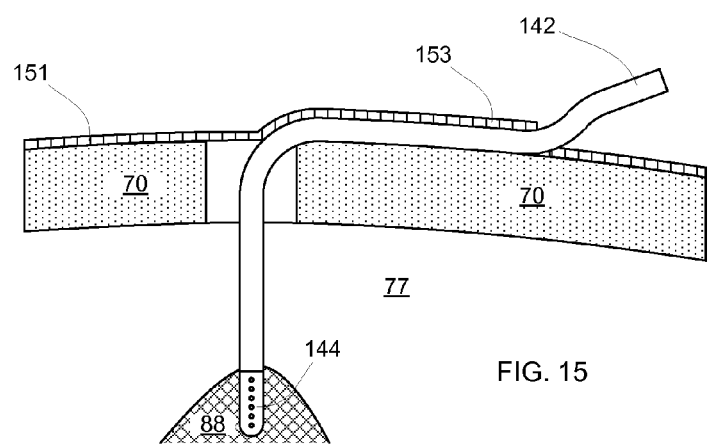
FIG. 15 is a diagrammatic sketch in a sectional view illustrating an intracranial catheter secured at the scalp.
Figure 21A:
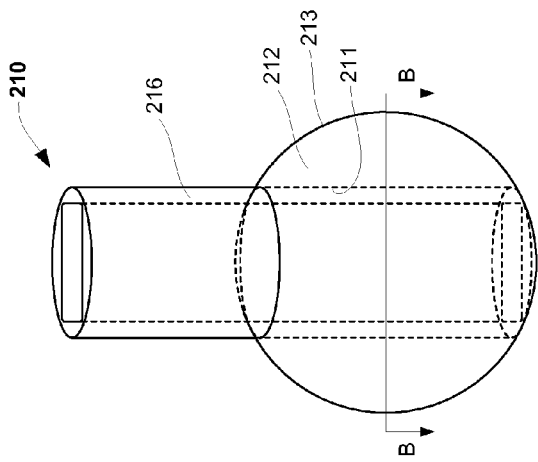
FIGS. 19A, 19B, 20A, 20B, 21A, 21B are diagrammatic sketches in three-dimensional view showing cranial access apparatus according to an embodiment of the invention.
Figure 21B:
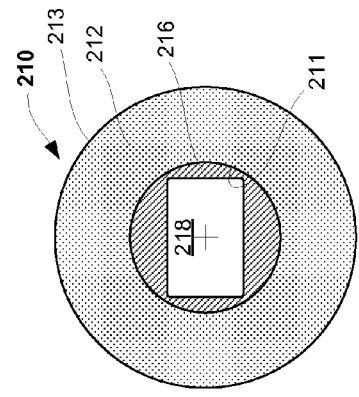
Figure 20A:
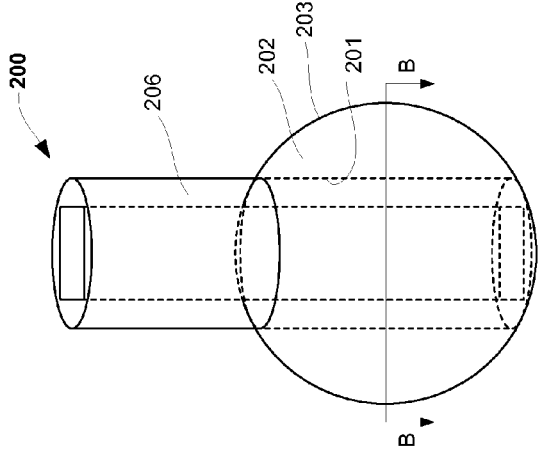
Figure 20B:
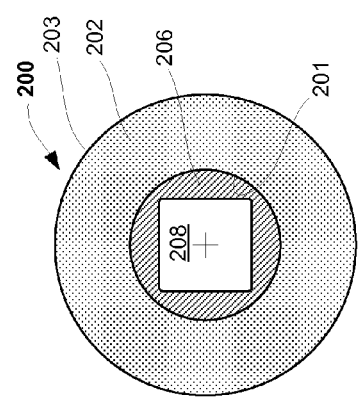

Following removal of the apparatus, customary surgical procedures may be followed for securing the ventricular drain, for example, or for establishing the distal aspects of a ventricular shunt. For example, as illustrated in FIG. 15, the catheter (or other device) may be tunneled subcutaneously under a flap 153 of skin and scalp 151 such that the distal end of the device emerges some distance away from the initial skin incision and cranial access site.

For other types of devices, such as a ventriculoscope or a needle, for example, the apparatus may if desired be left in place while the device is in place, until the procedure has been carried out.

Adapters may be configured to accommodate devices having other shapes, as illustrated by way of example in FIGS. 16A, 16B, 17A, 17B. The corresponding guidepiece is shown at 10 in FIG. 18. In these examples, as in the examples illustrated in FIGS. 10A, 10B, 11A, 11B, 12A, 12B, the adaptors are configured to fit within the guidepiece tube 16. In the examples shown by way of example in FIGS. 16A, 16B, 17A, 17B the adaptors are configured to receive devices having generally square (FIGS. 16A, 16B) or non-square rectangular (FIGS. 17A, 17B) cross-sections whose greatest dimensions are smaller than the inside diameter idt of the guidepiece tube. Accordingly, each of the adaptors 160, 170 has a circular cross-section, with an outside diameter 165, 175 respectively slightly less than the inside diameter idt of the corresponding guidepiece tube 16. Adaptor 160 has an inner surface 167 defining an axial bore having a square section, slightly larger than the square section of a device to be introduced through it; and adaptor 170 has an inner surface 177 defining an axial bore having a rectangular section, slightly larger than the rectangular section of a device to be introduced through it. Adaptors may be configured to accommodate devices having any of a variety of other cross-sections, such as generally triangular, for example, or non-circular round, for example.

The adaptor is introduced into the receiving end of the guidepiece tube 16 and advanced to a stop. Where a stop ring 14 is provided at the foot of the tube, and the adaptor is longer than (or the same length as) the guidepiece tube, the adaptor may rest upon the ring 14 at the foot of the tube. In the examples shown in these FIGs., at one end (a receiving end) of each adaptor tube are tabs 162, 162'; 172, 172' which project beyond the adaptor wall; where the adaptor is shorter than the guidepiece tube, or where a stop ring 14 is not provided, or to provide a redundant stop function, the tabs may rest upon the receiving end of the tube, preventing further advancement of the adaptor into the guidepiece.

As noted above with reference to FIGS. 1A, 1B, the guide tube is dimensioned to fit a cylindrical bore through the guidepiece body. That is, the outer diameter of the guide tube is approximately the same as the inner diameter of the bore. As noted above with reference to FIGS. 2 and 3, the receptacle parts are dimensioned to closely embrace the corresponding guidepiece body. As may be appreciated, guidepiece bodies may be dimensioned to match one (or a small number of) standardized receptacles. For example, there may be two standardized receptacles dimensioned respectively for pediatric and adult use; they may differ not only in the dimensions of the stem, but also in the spherical diameters of the respective guidepiece bodies to be used with them. The bore through any of such guidepiece bodies may be made large enough to accommodate the largest device whose use in connection with the apparatus is contemplated. For use with larger imaging devices requiring larger bore sizes, the diameter of the guidepiece ball 12 (FIG. 1A) may be increased, with corresponding increased diameters of the inner surfaces 33 and 23 of the receptacle cover 32 and cup 22, while the diameter of the receptacle stem 27 is kept at an appropriate size for use with a particular drill hole in the skull. Guide tubes adapted for use with such a standardized guidepiece body may be configured and dimensioned to receive devices of a variety of shapes and sizes, and sets of interchangeable guide tubes having a specified outside diameter may provided for each standard.

Examples are shown at 190, 200, 210 in FIGS. 19A, 19B, 20A, 20B, 21A, 21B. In each of these examples a guidepiece body 190, 200, 210 has a standard outside diameter 193, 203, 213, matching the inner diameter of a standard receptacle; and each has a bore through the center defining a cylindrical inner surface 191, 201, 211 and an alignment axis. A guide tube 196, 206, 216 in the bore has an outer surface (197 in FIG. 19A) having a diameter about the same as the inner diameter of the bore.

Figure 19A:
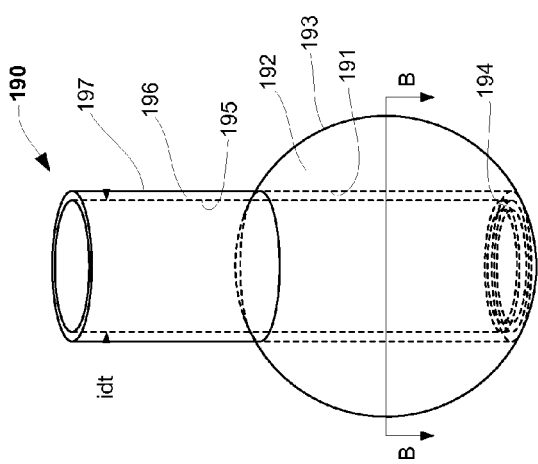
Figure 19B:
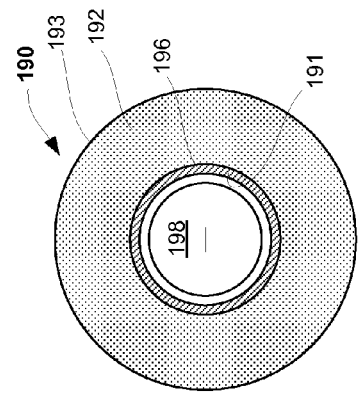

In the example of FIG. 19A, 19B, the guide tube 196 inner surface 195 defines a guide tube lumen 198 having a circular cross-section large enough to accommodate the largest device whose use in the guidepiece is contemplated. Imaging devices (such as ultrasound probes) having larger diameters than the drill hole in the skull can be used with such a guidepiece by selecting a guide tube having a suitable inner diameter. To accommodate smaller devices, or devices having cross-sectional shapes other than circular, various adapters configured to fit within the guide tube lumen 198 may be provided, generally as described with reference to FIGS. 10A, 10B, 11A, 11B, 12A, 12B, 16A, 16B, 17A, 17B, for example.

Or, alternatively, the bore itself in the guide tube may have a non-circular cross-section, as shown for example in FIGS. 20A, 20B, 21A, 21B. For example the lumen 208 of guide tube 206 in guidepiece 200 has a generally square cross-section, and the lumen 218 of guide tube 216 in guidepiece 210 has a generally non-square rectangular cross-section.

The inner diameter of the guide tube may be made proportionately much larger than the inner diameter of the stem; and the guidepiece body may be made larger to accommodate the larger stem, as illustrated by way of example in FIG. 22A. The guidepiece (body 212 and guide tube 216) is here shown rotated within the receptacle parts 222, 232. As in the examples described above, the diameter of the hole in the skull is about ¼ inch, and the stem 227 is dimensioned accordingly. In this example, the guide tube inner diameter is about twice as great as the diameter of the stem lumen 259. In FIG. 22A, a large probe 282 is shown seated within the guide tube, and the guidepiece is shown swiveled to near the maximum axial rotation permitted by the opening 234 in the cover 232. In this configuration some portion of the image field is obscured by the lower edge 255 of the inner surface 225 of the stem 227. A resulting image is illustrated in FIG. 22B, showing the target 228 unobscured by the "shadow" 222. At this juncture the receptacle can be tightened to lock the guidepiece 212, 216 and the probe 282 can be removed from the guide tube and replaced with an adaptor suited to receive a device to be placed at the target. The device is then placed, and the apparatus is withdrawn, generally as described above.

Figure 23C:
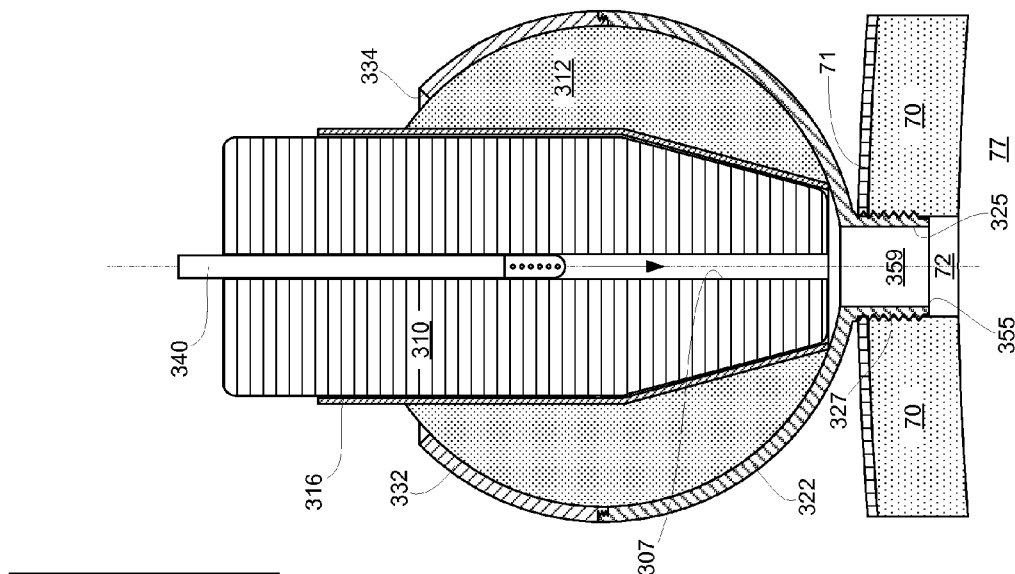
FIG. 23C is a diagrammatic sketch in sectional view showing deployment of an intracranial catheter using cranial access apparatus, according to an embodiment of the invention as shown in FIG. 23A.
Figure 23B:
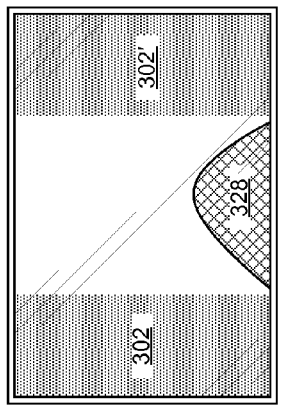
FIG. 23B is a diagrammatic sketch showing display of an image obtained by operation of an ultrasound imaging device as shown in FIG. 23A.
Figure 23A:
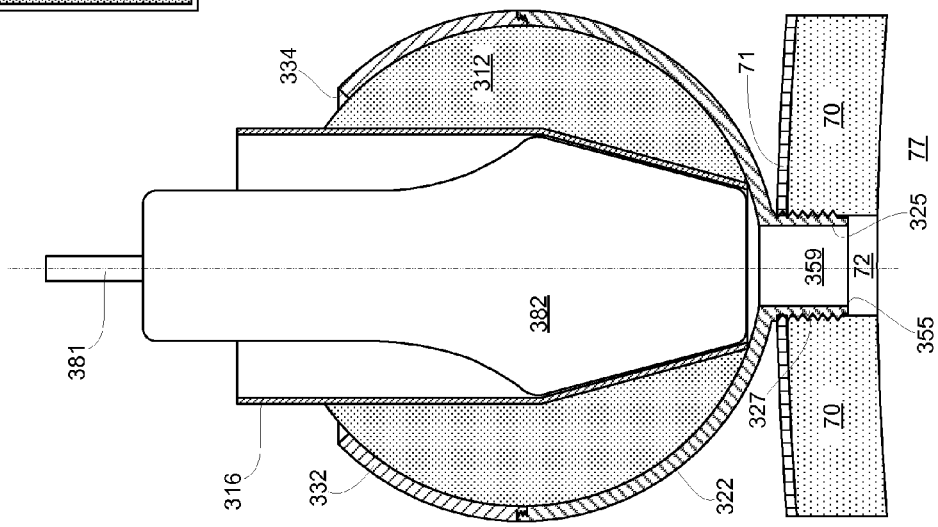
FIG. 23A is a diagrammatic sketch in a sectional view showing cranial access apparatus according to another embodiment of the invention.

The guidepiece may be configured to accept probes having any of a variety of shapes, as well as sizes. An example is shown in FIG. 23A. Here the guidepiece (body 312 and guide tube 316) is here shown within the receptacle parts 322, 332. As in the examples described above, the diameter of the hole in the skull is about ¼ inch, and the stem 327 is dimensioned accordingly. In this example, the guide tube is configured to conform to an end of a particular ultrasound probe 382 and accordingly its inner width is variable; near the foot the inner width of the guide tube is about twice as great as the diameter of the stem lumen 359. In FIG. 23A, an irregularly shaped large probe 382 is shown seated within the guide tube, and the guidepiece is shown with its axis nearly aligned with the axis of the receptacle. In this configuration portions of the image field are obscured by the lower edge 355 of the inner surface 325 of the stem lumen 327. A resulting image is illustrated in FIG. 23B, showing the target 328 unobscured by the "shadows" 302, 302'. As may be appreciated, the guide piece (carrying the probe) may be swiveled as described above to improve the alignment of the axis of the device with the optimal track to the target; the resulting image will have a wider "shadow" at one side and a narrower one at the other. At this juncture the receptacle can be tightened to lock the guidepiece 312, 316 and the probe 382 can be removed from the guide tube and, as shown in FIG. 23C, replaced with an adaptor 310 suited to fit within the guide tube 316 and to receive a device 340 to be placed at the target. The device is then placed, and the apparatus is withdrawn, generally as described above.

Other embodiments are within the claims.

For example, as noted above the guide tube and the guidepiece body may constitute a single part and, in such embodiments, the guide tube lumen constitutes the guidepiece lumen. The guide tube lumen is configured and dimensioned to receive and to maintain the position of the imaging device within the lumen during manipulation of the apparatus (e.g., while swiveling the guide piece) such that the imaging device axis is aligned with the guidepiece alignment axis. And, the guide tube lumen is configured and dimensioned to receive and to maintain the position of an adaptor within the lumen such that the adaptor bore is aligned with the guidepiece alignment axis. Whether the guide tube and the guidepiece body are separate parts or constitute a single part, the guide tube lumen may in some embodiments end near or flush with or inwardly from the outer surface of the guidepiece body, so long as the lumen provides sufficiently secure alignment of the imaging device or adaptor within it.

I claim:

1. Apparatus for directed cranial access to an intracranial site, comprising a guidepiece a receptacle, and an adaptor, wherein
    the receptacle comprises a lower part and an upper part, the lower receptacle part having a rim and a base and a hollow stem at the base adapted to be mounted in a hole in a skull, the upper receptacle part having a rim and an opening at the top, each part of the receptacle having an interior spherical surface, wherein the upper and lower receptacle parts can be joined at the rims to form an inner surface enclosing a generally spherical interior; and
    the guidepiece comprises a body having a spherical outer surface and a lumen through the center thereof, defining an alignment axis, the guidepiece being dimensioned to fit rotatably within the receptacle interior, the lumen being configured and dimensioned to accept an imaging device therein; and
    the adaptor is configured and dimensioned to be insertible within the guidepiece lumen, wherein the adaptor has a bore configured and dimensioned to accept a device to be placed at the site, and wherein an axis defined by the adaptor bore coincides with the alignment axis of the guidepiece.

2. The apparatus of claim 1, the guidepiece body further comprising a bore through the center thereof, and a guide tube in the bore, wherein a lumen in the guide tube comprises the guidepiece lumen.

3. The apparatus of claim 2 wherein the guidepiece body and the guide tube are a single part.

4. The apparatus of claim 2 wherein the guidepiece body and the guide tube are separate parts and the guidepiece is assembled by inserting the tube into the bore in the body.

5. The apparatus of claim 2 wherein an insert end of the guide tube extends away from the body.

6. The apparatus of claim 1 wherein the adaptor bore is cylindrical, having a diameter at least the same as a diameter of the device to be placed at the site.

7. The apparatus of claim 1 wherein the stem is dimensioned to be mounted in a hole in the skull having a diameter greater than the diameter of a device to be placed at the site, and less than 12.5 mm.

8. The apparatus of claim 7 wherein the stem is dimensioned to be mounted in a hole in the skull having a diameter greater than the diameter of a device to be placed at the site, and less than 6.4 mm.

9. The apparatus of claim 7 wherein the stem is dimensioned to be mounted in a hole in the skull having a diameter greater than 5 mm.

10. The apparatus of claim 1 wherein the stem is dimensioned to be mounted in a hole in the skull having a diameter in a range 6 mm to 8 mm.

11. The apparatus of claim 1 wherein the imaging device comprises an ultrasound probe.

12. The apparatus of claim 1 wherein the device to be placed is dimensioned so that the adaptor through which the device was inserted is fully removable over the entire length thereof.

13. The apparatus of claim 1 wherein the device to be placed at the site comprises a catheter.

14. The apparatus of claim 1 wherein the intracranial site comprises a cerebral ventricle, and the device to be placed at the site comprises a ventricular catheter.

15. The apparatus of claim 1 wherein the device to be placed comprises a cerebrospinal fluid shunt.

16. The apparatus of claim 1 wherein the intracranial site comprises a cerebral ventricle, and the device to be placed at the site comprises a ventricular shunt.

17. The apparatus of claim 1 wherein the apparatus can be assembled by joining the receptacle parts over the guidepiece body, an insertion end of the guidepiece lumen being situated within the top opening.

18. The apparatus of claim 17 wherein the rims of the receptacle parts are complementarily threaded, and wherein the apparatus can be assembled by screwing the receptacle parts together over the guidepiece body.

19. The apparatus of claim 1 wherein the receptacle parts can be tightened on the guidepiece body to restrict rotation of the guidepiece within the receptacle, reversibly locking the alignment axis in relation to the receptacle.

20. The apparatus of claim 1 wherein an inner width of the guidepiece lumen is at least about as great as the inner diameter of the stem.

21. The apparatus of claim 1, further comprising a stop that prevents an imaging device inserted into the guide tube from projecting inwardly beyond the outer table of the skull.

\* \* \* \* \*